(12) United States Patent
Griffith et al.

(10) Patent No.: US 6,194,578 B1
(45) Date of Patent: Feb. 27, 2001

(54) DIPEPTIDE DERIVATIVES

(75) Inventors: David A. Griffith, Old Saybrook; Brian S. Bronk, Gales Ferry, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/348,449

(22) Filed: Jul. 7, 1999

Related U.S. Application Data

(60) Provisional application No. 60/109,219, filed on Nov. 20, 1998.

(51) Int. Cl.[7] .................. C07D 487/00; C07D 403/00

(52) U.S. Cl. ............................. 544/349; 544/373

(58) Field of Search .................. 514/252.1, 252.13; 544/349, 373

(56) References Cited

FOREIGN PATENT DOCUMENTS

9858947 * 6/1998 (WO) .

* cited by examiner

Primary Examiner—Mukund J. Shah
Assistant Examiner—Sudhaker B. Patel
(74) Attorney, Agent, or Firm—Peter C. Richardson; Paul H. Ginsburg; Jolene W. Appleman

(57) ABSTRACT

This invention is directed to compounds of the Formula

I

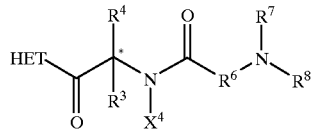

and the pharmaceutically-acceptable salts thereof, where the substituents are as defined in the Specification, which are growth hormone secretogogues and which increase the level of endogenous growth hormone. The compounds of this invention are therapeutically effective in treating osteoporosis and/or frailty, congestive heart failure, frailty associated with aging, obesity; accelerating bone fracture repair, attenuating protein catabolic response after a major operation, reducing cachexia and protein loss due to chronic illness, accelerating wound healing, or accelerating the recovery of burn patients or patients having undergone major surgery; improving muscle strength, mobility, maintenance of skin thickness, metabolic homeostasis or renal homeostasis. The compounds of the present invention are also useful in treating osteoporosis and/or frailty when used in combination with: a bisphosphonate compound such as alendronate; estrogen, premarin, and optionally progesterone; an estrogen agonist or antagonist; or calcitonin, and pharmaceutical compositions useful therefor. Further, the present invention is directed to pharmaceutical compositions therapeutically effective for increasing the endogenous production or release of growth hormone in a human or other animal which comprises an effective amount of a compound of the present invention and a growth hormone secretagogue selected from GHRP-6, Hexarelin, GHRP-1, growth hormone releasing factor (GRF), IGF-1, IGF-2 or B-HT920. The invention is also directed to intermediates useful in the preparation of compounds of Formula I.

59 Claims, No Drawings

DIPEPTIDE DERIVATIVES

This application claims the benefit of U.S. Provisional Application No. 60/109,219 filed Nov. 20, 1998.

This invention relates to dipeptide compounds which are growth hormone secretagogues and are useful for the treatment and prevention of osteoporosis and/or frailty, insulin resistance in mammals, congestive heart failure, obesity, accelerating bone fracture repair and accelerating wound repair.

BACKGROUND OF THE INVENTION

Growth hormone (GH), which is secreted from the pituitary gland, stimulates growth of all tissues of the body that are capable of growing. In addition, growth hormone is known to have the following basic effects on the metabolic processes of the body:

1. Increased rate of protein synthesis in substantially all cells of the body;
2. Decreased rate of carbohydrate utilization in cells of the body; and
3. Increased mobilization of free fatty acids and use of fatty acids for energy.

Deficiency in growth hormone results in a variety of medical disorders. In children, it causes dwarfism. In adults, the consequences of acquired GH deficiency include profound reduction in lean body mass and concomitant increase in total body fat, particularly in the truncal region. Decreased skeletal and cardiac muscle mass and muscle strength lead to a significant reduction in exercise capacity. Bone density is also reduced. Administration of exogenous growth hormone has been shown to reverse many of the metabolic changes. Additional benefits of therapy have included reduction in LDL cholesterol and improved psychological well-being. This is described in U.S. Patent No. 60/050,764 incorporated by reference.

SUMMARY OF THE INVENTION

The present invention provides novel chemical compounds of the following Formula I

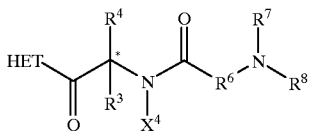

or a pharmaceutically acceptable salt or prodrug thereof, wherein:

HET is a heterocyclic moiety selected from the group consisting of

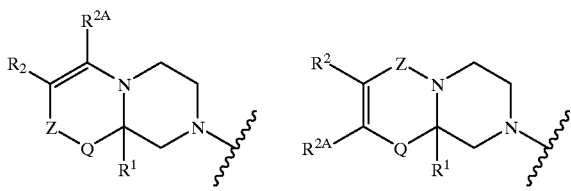

-continued

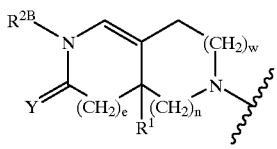

e is 0 or 1;

n and w are each independently 0, 1, or 2, provided that w and n cannot both be 0 at the same time;

Y is oxygen or sulfur;

$R^2$ is selected from the group consisting of hydrogen, fluoro, and ($C_1$–$C_5$)alkyl optionally substituted with 1–5 halo groups;

$R^{2A}$ is selected from the group consisting of hydrogen, $SX^6$, $OX^6$, —$N(X^6)(X^6)$, ($C_1$–$C_8$)alkyl, —($C_0$–$C_3$)alkyl-($C_1$–$C_7$)cycloalkyl, and -($C_0$–$C_3$)alkyl-$A^1$, where the alkyl groups and the cycloalkyl groups are optionally substituted with hydroxy, thio, $C(O)OX^6$, $C(O)N(X^6)(X^6)$, $SO_2N(X^6)(X^6)$, $S(O)_m(C_1$–$C_6)$alkyl, $C(O)A^1$, $C(O)(X^6)$, CN or 1–5 halo groups;

Q is a covalent bond or $CR^9R^{10}$;

Z is C=O, C=S or $S(O)_2$;

$R^{2B}$ is hydrogen, ($C_1$–$C_8$)alkyl, ($C_0$–$C_3$)alkyl-($C_3$–$C_8$)cycloalkyl, -($C_1$–$C_4$)alkyl-$A^1$ or $A^1$; where the alkyl groups and the cycloalkyl groups in the definition of $R^{2B}$ are optionally substituted with hydroxyl, $C(O)OX^6$, —$C(O)N(X^6)(X^6)$, —$N(X^6)(X^6)$, —$S(O)_m(C_1$–$C_6)$alkyl, $C(O)A^1$, —$C(O)(X^6)$, $CF_3$, CN or 1, 2 or 3 halogen;

$R^1$ is hydrogen, —CN, —$(CH_2)_qN(X^6)C(O)X^6$, —$(CH_2)_qN(X^6)C(O)(CH_2)_t$—$A^1$, —$(CH_2)_qN(X^6)S(O)_2(CH_2)_t$—$A^1$, —$(CH_2)_qN(X^6)S(O)_2X^6$, —$(CH_2)_qN(X^6)C(O)N(X^6)(CH_2)_t$—$A^1$, —$(CH_2)_qN(X^6)C(O)N(X^6)(X^6)$, —$(CH_2)_qC(O)N(X^6)(X^6)$, —$(CH_2)_qC(O)N(X^6)(CH_2)_t$—$A^1$, —$(CH_2)_qC(O)OX^6$, —$(CH_2)_qC(O)O(CH_2)_t$—$A^1$, —$(CH_2)_qOX^6$, —$(CH_2)_qOC(O)X^6$, —$(CH_2)_qOC(O)(CH_2)_t$—$A^1$, —$(CH_2)_qOC(O)N(X^6)(CH_2)_t$—$A^1$, —$(CH_2)_qOC(O)N(X^6)(X^6)$, —$(CH_2)_qC(O)X^6$, —$(CH_2)_qC(O)(CH_2)_t$—$A^1$, —$(CH_2)_qN(X^6)C(O)OX^6$, —$(CH_2)_qN(X^6)S(O)_2N(X^6)(X^6)$, —$(CH_2)_qS(O)_mX^6$, —$(CH_2)_qS(O)_m(CH_2)_t$—$A^1$, —$(C_1$–$C_{10})$alkyl, —$(CH_2)_t$—$A^1$, —$(CH_2)_q$—($C_3$–$C_7$)cycloalkyl, —$(CH_2)_q$—$Y^1$-($C_1$–$C_6$)alkyl, —$(CH_2)_q$—$Y^1$—$(CH_2)_t$—$A^1$ or —$(CH_2)_q$—$Y^1$—$(CH_2)_t$—($C_3$–$C_7$)cycloalkyl;

wherein the alkyl and cycloalkyl groups in the definition of $R^1$ are optionally independently substituted with ($C_1$–$C_4$)alkyl, hydroxy, ($C_1$–$C_4$)alkoxy, carboxyl, —$CONH_2$, —$S(O)_m(C_1$–$C_6)$alkyl, —$CO_2(C_1$–$C_4$)alkyl ester, 1H-tetrazol-5-yl or 1, 2 or 3 fluoro groups;

$Y^1$ is O, $S(O)_m$, —$C(O)NX^6$—, —CH=CH—, —C≡C—, —$N(X^6)C(O)$—, —$C(O)NX^6$—, —$C(O)O$—, —$OC(O)N(X^6)$— or —$OC(O)$—;

q is 0, 1, 2, 3 or 4, with the proviso that q cannot be 0 when $(CH_2)_q$ is attached to N or O;

t is 0, 1, 2 or 3;

m is 1 or 2;

$R^3$ is selected from the group consisting of $A^1$, ($C_1$–$C_{10}$)alkyl, -($C_1$–$C_6$)alkyl-$A^1$, —($C_1$–$C_6$)alkyl-($C_3$–$C_7$)cycloalkyl, -($C_1$–$C_5$)alkyl-$X^1$-($C_1$–$C_5$)alkyl, -($C_1$–$C_5$)alkyl-$X^1$—($C_0$–$C_5$)alkyl-$A^1$ and -($C_1$–$C_5$)alkyl-$X^1$-($C_1$–$C_5$)alkyl-($C_3$–$C_7$)cycloalkyl;

where the alkyl groups in the definition of $R^3$ are optionally substituted with —$S(O)_m(C_1$–$C_6)$alkyl, —$C(O)OX^3$, 1, 2, 3, 4 or 5 independently selected halo groups or 1, 2 or 3 independently selected —$OX^3$ groups;

$X^1$ is O, $S(O)_m$, —$N(X^2)C(O)$—, —$C(O)N(X^2)$—, —$OC(O)$—, —$C(O)O$—, —$CX^2$=$CX$—, —$N(X^2)C(O)O$, —$OC(O)N(X^2)$— or —C≡C—;

$X^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with $—S(O)_m(C_1-C_6)$alkyl, $—C(O)OX^3$, 1 to 5 halo groups or 1–3 $OX^3$ groups;

$R^4$ is hydrogen, $(C_1-C_6)$alkyl or $(C_3-C_7)$cycloalkyl, or $R^4$ is taken together with $R^3$ and the carbon atom to which they are attached and form $(C_5-C_7)$cycloalkyl, $(C_5-C_7)$cycloalkenyl, a partially saturated or fully saturated 4- to 8-membered ring having 1 to 4 heteroatoms independently selected from the group consisting of oxygen, sulfur and nitrogen, or $R^4$ and $R^3$ can be taken together to form a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;

$X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring;

$R^6$ is a bond or

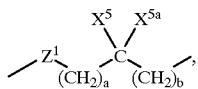

or $—(CR^aR^b)_a—E—(CR^1R^b)_b—$;
where the $—(CR^aR^b)_a—$ group is attached to the carbonyl carbon of the amide group of the compound of Formula I and the $—(CR^aR^b)_b$ group is attached to the terminal nitrogen atom of the compound of Formula I;

E is $—O—$, $—S—$, $—CH=CH—$,

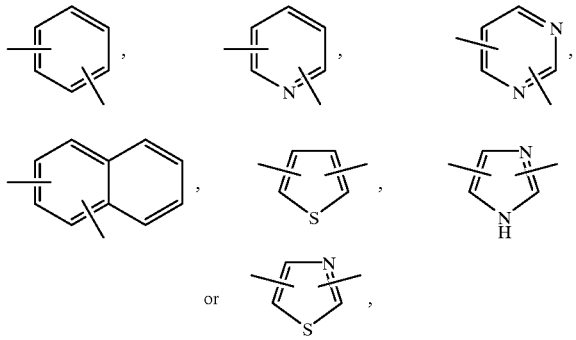

which is optionally substituted with halo, hydroxy, $—N(R^c)(R^c)$, $(C_1-C_6)$alkyl or $(C_1-C_6)$alkoxy;

$R^a$ and $R^b$ are independently hydrogen, $(C_1-C_6)$alkyl, trifluoromethyl, phenyl or substituted $(C_1-C_6)$alkyl where the substituents are imidazolyl, naphthyl, phenyl, indolyl, p-hydroxyphenyl, $—OR^c$, $S(O)_mR^c$, $C(O)OR^c$, $(C_3-C_7)$cycloalkyl, $—N(R^c)(R^c)$, $—C(O)N(R^c)(R^c)$; or $R^a$ and $R^b$ may independently be joined to one or both of $R^7$ or E (where E is other than O, S or $—CH=CH—$) to form an alkylene bridge between the terminal nitrogen and the alkyl portion of the $R^a$ or $R^b$ and the $R^7$ or E group, wherein the bridge contains 1 to 8 carbon atoms; or $R^a$ and $R^b$ may be joined to one another to form a $(C_3-C_7)$cycloalkyl;

$R^c$ is hydrogen or $(C_1-C_6)$alkyl;

a and b are independently 0, 1, 2 or 3, with the proviso that if E is $—O—$ or $—S—$, y is other than 0 or 1 and with the further proviso that if E is $—CH=CH—$, y is other than 0;

$X^5$ and $X^{5a}$ are each independently selected from the group consisting of hydrogen, $CF_3$, $A^1$ and optionally substituted $(C_1-C_6)$alkyl;

the optionally substituted $(C_1-C_6)$alkyl in the definition of $X^5$ and $X^{5a}$ is optionally substituted with a substituent selected from the group consisting of $A^1$, $OX^2$, $—S(O)_m(C_1-C_6)$alkyl, $—C(O)OX^2$, $(C_3-C_7)$cycloalkyl, $—N(X^2)(X^2)$ and $—C(O)N(X^2)(X^2)$;

or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then only one of $X^5$ or $X^{5a}$ is on the carbon atom and only one of $R^7$ or $R^8$ is on the nitrogen atom and further provided that when two alkylene bridges are formed then $X^5$ and $X^{5a}$ cannot be on the carbon atom and $R^7$ and $R^8$ cannot be on the nitrogen atom;

or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;

or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$Z^1$ is a bond, O or $N—X^2$, provided that when a and b are both O then $Z^1$ is not $N—X^2$ or O;

$R^7$ and $R^8$ are each independently hydrogen or optionally substituted $(C_1-C_6)$alkyl;

where the optionally substituted $(C_1-C_6)$alkyl in the definition of $R^7$ and $R^8$ is optionally independently substituted with $A^1$, $—C(O)O—(C_1-C_6)$alkyl, $—S(O)_m(C_1-C_6)$alkyl, 1 to 5 halo groups, 1 to 3 hydroxy groups, 1 to 3 $—O—C(O)(C_1-C_{10})$alkyl groups or 1 to 3 $(C_1-C_6)$alkoxy groups; or $R^7$ and $R^8$ can be taken together to form $—(CH_2)_r—L—(CH_2)_r—$; where L is $C(X^2)(X^2)$, $S(O)_m$ or $N(X^2)$;

$R^9$ and $R^{10}$ are each independently selected from the group consisting of hydrogen, fluoro, hydroxy and $(C_1-C_5)$ alkyl optionally independently substituted with 1–5 halo groups;

$A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully saturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, on one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, $—OX^6$, $—C(O)N(X^6)(X^6)$, $—C(O)OX^6$, oxo, $(C_1-C_6)$alkyl, nitro, cyano, benzyl, $—S(O)_m(C_1-C_6)$alkyl, 1H-tetrazol-5-yl, phenyl, phenoxy, phenylalkyloxy, halophenyl, methylenedioxy, —N($X^6$)($X^6$), —N($X^6$)C(O)($X^6$), —S(O)$_2$N($X^6$)($X^6$), —N($X^6$)S(O)$_2$-phenyl, —N($X^6$)S(O)$_2X^6$, —CON$X^{11}X^{12}$, —S(O)$_2$N$X^{11}X^{12}$, —N$X^6$S(O)$_2X^{12}$, —N$X^6$CON$X^{11}X^{12}$, —N$X^6$S(O)$_2$N$X^{11}X^{12}$, —N$X^6$C(O)$X^{12}$, imidazolyl, thiazolyl and tetrazolyl, provided that if $A^1$ is optionally substituted with methylenedioxy then it can only be substituted with one methylenedioxy;

where $X^{11}$ is hydrogen or optionally substituted ($C_1$–$C_6$)alkyl;

the optionally substituted ($C_1$–$C_6$)alkyl defined for $X^{11}$ is optionally independently substituted with phenyl, phenoxy, ($C_1$–$C_6$)alkoxycarbonyl, —S(O)$_m$($C_1$–$C_6$)alkyl, 1 to 5 halo groups, 1 to 3 hydroxy groups, 1 to 3 ($C_1$–$C_{10}$)alkanoyloxy groups or 1 to 3 ($C_1$–$C_6$)alkoxy groups;

$X^{12}$ is hydrogen, ($C_1$–$C_6$)alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, $CH_3$, $OCH_3$, $OCF_3$ and $CF_3$;

or $X^{11}$ and $X^{12}$ are taken together to form —(CH$_2$)$_r$—$L^1$—(CH$_2$)$_r$—;

$L^1$ is C($X^2$)($X^2$), O, S(O), or N($X^2$);

r for each occurrence is independently 1, 2 or 3;

$X^2$ for each occurrence is independently hydrogen, optionally substituted ($C_1$–$C_6$)alkyl or optionally substituted ($C_3$–$C_7$)cycloalkyl, where the optionally substituted ($C_1$–$C_6$)alkyl and optionally substituted ($C_3$–$C_7$)cycloalkyl in the definition of $X^2$ are optionally independently substituted with —S(O)$_m$($C_1$–$C_6$)alkyl, —C(O)O$X^3$, 1 to 5 halo groups or 1–3 O$X^3$ groups;

$X^3$ for each occurrence is independently hydrogen or ($C_1$–$C_6$)alkyl;

$X^6$ for each occurrence is independently hydrogen, optionally substituted ($C_1$–$C_6$)alkyl, ($C_2$–$C_6$)halogenated alkyl, optionally substituted ($C_3$–$C_7$)cycloalkyl, ($C_3$–$C_7$)-halogenated cycloalkyl, where optionally substituted ($C_1$–$C_6$)alkyl and optionally substituted ($C_3$–$C_7$)cycloalkyl in the definition of $X^6$ is optionally independently mono- or di-substituted with ($C_1$–$C_4$)alkyl, hydroxy, ($C_1$–$C_4$)alkoxy, carboxyl, $CONH_2$, S(O)$_m$($C_1$–$C_6$)alkyl, carboxylate ($C_1$–$C_4$) alkyl ester or 1H-tetrazol-5-yl; or when there are two $X^6$ groups on one atom and both $X^6$ are independently ($C_1$–$C_6$) alkyl, the two ($C_1$–$C_6$)alkyl groups may be optionally joined and, together with the atom to which the two $X^6$ groups are attached, form a 4- to 9- membered ring optionally having oxygen, sulfur or N$X^7$ as a ring member;

$X^7$ is hydrogen or ($C_1$–$C_6$)alkyl optionally substituted with hydroxy;

m for each occurrence is independently 0, 1 or 2;

with the proviso that:

$X^6$ and $X^{12}$ cannot be hydrogen when attached to C(O) or S(O)$_2$ in the form C(O)$X^6$, C(O)$X^{12}$, S(O)$_2X^6$ or S(O)$_2X^{12}$; and when $R^6$ is a bond then L is N($X^2$) and each r in the definition —(CH$_2$)$_r$—L—(CH$_2$)$_r$— is independently 2 or 3.

A preferred group of the foregoing compounds, designated the A group compounds, are those compounds of Formula I wherein $R^4$ is hydrogen or methyl; $X^4$ is hydrogen;

$R^6$ is

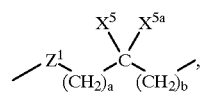

where $Z^1$ is a bond and a is 0 or 1; $X^5$ and $X^{5a}$ are each independently selected from the group consisting of hydrogen, $CF_3$, phenyl and optionally substituted ($C_1$–$C_6$) alkyl;

where the optionally substituted ($C_1$–$C_6$)alkyl in the definition of $X^5$ and $X^{5a}$ is optionally substituted with O$X^2$ or $A^1$;

where $A^1$ in the definition of $X^5$ and $X^{5a}$ is imidazolyl, phenyl, indolyl, p-hydroxyphenyl, ($C_5$–$C_7$)cycloalkyl, —S(O)$_m$($C_1$–$C_6$)alkyl, —N($X^2$)($X^2$) or —C(O)N($X^2$)($X^2$);

$R^7$ is hydrogen or ($C_1$–$C_3$)alkyl;

or $X^5$ and $R^7$ are taken together and form a ($C_1$–$C_5$) alkylene bridge; and $R^8$ is hydrogen or ($C_1$–$C_3$)alkyl optionally substituted with one or two hydroxy groups.

A group of compounds which is preferred among the A group compounds, designated the B group, are those compounds of the A group wherein b is 0; $X^5$ and $X^{5a}$ are each independently selected from the group consisting of hydrogen, ($C_1$–$C_3$)alkyl and hydroxy($C_1$–$C_3$)alkyl; and $R^3$ is selected from the group consisting of thienyl-CH$_2$—O—CH$_2$—, pyridyl-CH$_2$—O—CH$_2$—, thiazolyl-CH$_2$—O—CH$_2$—, 1-indolyl-CH$_2$—, 2-indolyl-CH$_2$—, 3-indolyl-CH$_2$—, 1-naphthyl-CH$_2$, 2-naphthyl-CH$_2$—, 1-benzimidazolyl-CH$_2$—, 2-benzimidazolyl-CH$_2$—, phenyl-($C_1$–$C_4$)alkyl, 2-pyridyl-($C_1$–$C_4$)alkyl—, 3-pyridyl-($C_1$–$C_4$)alkyl-, 4-pyridyl-($C_1$–$C_4$)alkyl-, phenyl-CH$_2$—S—CH$_2$—, thienyl-($C_1$–$C_4$)alkyl-, phenyl-($C_0$–$C_3$)alkyl-O—CH$_2$—, phenyl-CH$_2$—O-phenyl-CH$_2$—, phenyl-O—CH$_2$—CH$_2$— and 3-benzothienyl-CH$_2$—;

where the aryl portion(s) of the groups defined for $R^3$ are each optionally substituted with one to three substituents, each substituent being independently selected from the group consisting of methylenedioxy, F, Cl, $CH_3$, $OCH_3$, $OCF_3$, $OCF_2H$ and $CF_3$.

A group of compounds which is preferred among the B group compounds, designated the C group, are those compounds of the B group wherein $R^4$ is hydrogen; a is 0;

$X^5$ and $X^{5a}$ are each independently selected from the group consisting of hydrogen, methyl or hydroxymethyl, provided that when $X^5$ is hydrogen then $X^{5a}$ is not hydrogen;

$R^7$ and $R^8$ are each hydrogen; and $R^3$ is selected from the group consisting of 3-indolyl-CH$_2$—, 1-naphthyl-CH$_2$—, 2-naphthyl-CH$_2$—, phenyl-($C_1$–$C_4$)alkyl-, 2-pyridyl-($C_1$–$C_4$)alkyl-, 3-pyridyl-($C_1$–$C_4$) alkyl-, 4-pyridyl-($C_1$–$C_4$)alkyl-, phenyl-CH$_2$—S—CH$_2$—, thienyl-($C_2$–$C_4$)alkyl-, phenyl-($C_0$–$C_3$)alkyl-O—CH$_2$—, 3-benzothienyl-CH$_2$—, thienyl-CH$_2$—O—CH$_2$—, thiazolyl-CH$_2$—O—CH$_2$—, pyridyl-CH$_2$—O—CH$_2$— and phenyl-O—CH$_2$—CH$_2$—;

where the aryl portion(s) of the groups defined for $R^3$ are each optionally substituted with one to three substituents, each substituent being independently selected from the group consisting of methylenedioxy, F, Cl, $CH_3$, $OCH_3$, $OCF_3$, $OCF_2H$ and $CF_3$.

A group of compounds which is preferred among the C group compounds, designated the D group, are those compounds of the C group wherein $R^1$ is —(CH$_2$)$_t$—$A^1$, —(CH$_2$)$_q$—($C_3$–$C_7$)cycloalkyl or ($C_1$–$C_{10}$)alkyl;

$A^1$ in the definition of $R^1$ is phenyl, pyridyl, thiazolyl or thienyl, optionally substituted with one to three substituents, each substituent being independently selected from the group consisting of F, Cl, $CH_3$, $OCH_3$, $OCF_2H$, $OCF_3$ and $CF_3$;

the cycloalkyl and alkyl groups in the definition of $R^1$ are optionally substituted with $(C_1-C_4)$alkyl, hydroxy, $(C_1-C_4)$ alkoxy or 1 to 3 fluoro atoms;

q is 1 or 2; t is 1 or 2;

$R^3$ is phenyl-$CH_2$—O—$CH_2$—, phenyl-$CH_2$—S—$CH_2$—, pyridyl-$CH_2$—O—$CH_2$—, thienyl-$CH_2$—O—$CH_2$—, thiazolyl-$CH_2$—O—$CH_2$—, phenyl-$(CH_2)_3$— or 3-indolyl-$CH_2$—;

where the carbon atom bearing the substituent $R^3$ is of the (R)-configuration;

where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$; and $X^5$ and $X^{5a}$ are each methyl.

A group of compounds which is preferred among the D group compounds designated the E group, are those compounds of the D group wherein HET' is

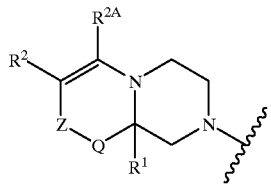

A group of compounds which is preferred among the E group compounds, designated the F group, are those compounds of the E group wherein Z is C=O; and Q is a covalent bond;

A group of compounds which is preferred among the F group compounds designated the G group, are those compounds of the F group wherein $R^2$ is hydrogen or $(C_1-C_3)$ alkyl where the alkyl is optionally substituted with 1–3 fluoro groups;

$R^{2A}$ is —$SX^6$;

$X^6$ is $(C_1-C_3)$alkyl or $(C_3-C_6)$ cycloalkyl, where the alkyl and cycloalkyl may be optionally substituted with one to three halogens.

A group of compounds which is preferred among the G group designated the H group, are those compounds of the G group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and $R^3$ is selected form the group consisting of 3-indolyl-$CH_2$—, phenyl—$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

Preferred compounds of the H group are the 8a(R,S),1(R) diastereomeric mixture, the 8a(R),1(R) diastereomer or the 8a(S),1(R) diastereomer of 2-amino-N-{1(R)-benzyloxymethyl-2-[8a-(4-fluoro-benzyl)-6-methylsulfanyl-8-oxo-3,4,8,8a-tetrahydro-1H-pyrrolo[1,2-a]pyrazin-2-yl]-2-oxo-ethyl}-2-methyl-propionamide.

Another group of compounds which is preferred among the E group, designated the I group, are those compounds of the E group wherein $R^2$ is hydrogen or $(C_1-C_3)$alkyl where the alkyl is optionally substituted with 1–3 fluoro groups;

$R^1$ is —$N(X^6)(X^6)$;

$X^6$ for each occurrence is independently hydrogen, optionally substituted $(C_1-C_3)$alkyl, $(C_2-C_3)$fluoronated alkyl, optionally substituted $(C_3-C_6)$cycloalkyl, $(C_3-C_6)$ fluorinated cycloalkyl, where when there are two $X^6$ groups on one atom and both $X^6$ are independently $(C_1-C_3)$alkyl, the two $(C_1-C_3)$alkyl groups may be optionally joined and, together with the atom to which the two $X^6$ groups are attached, form a 4- to 6-membered ring optionally having oxygen as a ring member.

A group of compound which is preferred among the I group compounds, designated the J group, are those compounds of the I group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and $R^3$ is selected form the group consisting of 3-indolyl-$CH_2$—, phenyl—$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

Preferred compounds of the J group are the 8a(R,S),1(R) diastereomeric mixture, the 8a(R),1(R) diastereomer or the 8a(S),1(R) diastereomer of the compound selected from the group consisting of 2-amino-N-{1(R)-benzyloxymethyl-2-[8a-(4-fluoro-benzyl)-8-oxo-6-pyrrolidin-1-yl-3,4,8,8a-tetrahydro-1H-pyrrolo[1,2-a]pyrazin-2-yl]-2-oxo-ethyl}-2-methyl-propionamide or 2-amino-N-{1(R)-benzyloxymethyl-2-[8a-(4-fluoro-benzyl)-6-morpholin-4-yl-8-oxo-3,4,8,8a-tetrahydro-1H-pyrrolo[1,2-a]pyrazin-2-yl]-2-oxo-ethyl}-2-methyl-propionamide.

Another group of compounds which is preferred among E group compounds, designated the K group, are those compounds of the E group wherein $R^2$ is hydrogen or $(C_1-C_3)$ alkyl where the alkyl is optionally substituted with 1–3 fluoro groups;

$R^{2A}$ is hydrogen, -$(C_1-C_4)$alkyl, -$(C_0-C_2)$alkyl-$(C_1-C_6)$ cycloalkyl, -$(C_0-C_2)$alkyl-$A^1$ where the alkyl groups are optionally substituted with 1–3 fluoro groups;

$A^1$ is phenyl, pyridyl or thiazolyl optionally substituted with one to two substituents, each substituent being independently selected from the group consisting of F, Cl, $CH_3$, $OCF_2H$, $OCF_3$, and $CF_3$.

A group of compounds which is preferred among the K group compounds, designated the L group, are those the K group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and $R^3$ is selected form the group consisting of 3-indolyl-$CH_2$—, phenyl—$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

A group of compounds which is preferred among the L group compounds, are the 8a(R,S),1(R) diastereomeric mixture, the 8a(R),1(R) diastereomer or the 8a(S),1(R) diastereomer of the compound selected from the group consisting of 2-amino-N-{1(R)-benzyloxymethyl-2-[8a-(4-fluoro-benzyl)-8-oxo-3,4,8,8a-tetrahydro-1H-pyrrolo[1,2-a]pyrazin-2-yl]-2-oxo-ethyl}-2-methyl-propionamide, 2-amino-N-[1(R)-benzyloxymethyl-2-oxo-2-(8-oxo-6-pyridin-2-yl-8a-pyridin-2-ylmethyl-3,4,8,8a-tetrahydro-1H-pyrrolo[1,2-a]pyrazin-2-yl)-ethyl]-2-methyl-propionamide, or 2-amino-N-[2-(8a-benzyl-6-ethyl-8-oxo-3,4,8,8a-tetrahydro-1H-pyrrolo[1,2-a]pyrazin-2-yl)-1(R)-benzyloxymethyl-2-oxo-ethyl]-2-methyl-propionamide.

Another group of compounds preferred among the E group compounds, designated the N group, are those wherein HET

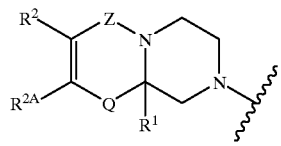

Another group of compounds which is preferred among the E group compounds, designated the O group, are those compounds of the E group wherein Z is C=O; Q is a covalent bond;

A group of compounds which is preferred among the O group compounds, designated the P group, are those compounds of the O group wherein $R^2$ is hydrogen or $(C_1-C_3)$ alkyl where the alkyl is optionally substituted with 1–3 fluoro groups;

$R^{2A}$ is —$OX^6$;

$X^6$ is $(C_1-C_3)$alkyl or $(C_3-C_6)$ cycloalkyl, where the alkyl and cycloalkyl may be optionally substituted with one to three halogens.

A group of compounds which preferred among the P group designated the Q group, are those compounds of the P group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and $R^3$ is selected form the group consisting of 3-indolyl-$CH_2$—, phenyl—$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

A group compounds which is preferred among the Q group, designated the R group compounds, are those compounds of the Q group wherein the compounds are the 8a(R,S),1(R) diastereomeric mixture, the 8a(R),1(R) diastereomer or the 8a(S),1(R) diastereomer of the compound selected from the group consisting of 2-amino-N-[1(R)-benzyloxymethyl-2-(8-methoxy-6-oxo-8a-pyridin-2-ylmethyl-3,4,6,8a-tetrahydro-1H-pyrrolo[1,2-a]pyrazin-2-yl)-2-oxo-ethyl]-2-methyl-propionamide, 2-amino-N-{1(R)-benzyloxymethyl-2-[8a-(4-fluoro-benzyl)-8-methoxy-6-oxo-3,4,6,8a-tetrahydro-1H-pyrrolo[1,2-a]pyrazin-2-yl]-2-oxo-ethyl)-2-methyl-propionamide or 2-amino-N-{1(R)-benzyloxymethyl-2-[8a-(4-fluoro-benzyl)-8-methoxy-7-methyl-6-oxo-3, 4,6,8a-tetrahydro-1H-pyrrolo[1,2-a] pyrazin-2-yl]-2-oxo-ethyl}-2-methyl-propionamide.

Another group of compounds which is preferred among the O group compounds, designated the S group, are those compounds of the O group wherein $R^2$ is hydrogen, —$(C_1-C_4)$alkyl, —$(C_0-C_2)$alkyl—$(C_1-C_6)$cycloalkyl, —$(C_0-C_2)$alkyl-$A^1$ where the alkyl groups are optionally substituted with 1–3 fluoro groups;

$A^1$ is phenyl, pyridyl or thiazolyl optionally substituted with one to two substituents, each substituent being independently selected from the group consisting of F, Cl, $CH_3$, $OCF_2H$, $OCF_3$, and $CF_3$;

$R^1$ is —$N(X^6)(X^6)$;

$X^6$ for each occurrence is independently hydrogen, optionally substituted $(C_1-C_3)$alkyl, $(C_2-C_3)$fluoronated alkyl, optionally substituted $(C_3-C_6)$cycloalkyl, $(C_3-C_6)$ fluoronated cycloalkyl, where when there are two $X^6$ groups on one atom and both $X^6$ are independently $(C_1-C_3)$alkyl, the two $(C_1-C_3)$alkyl groups may be optionally joined and, together with the atom to which the two $X^6$ groups are attached, form a 4- to 6-membered ring optionally having oxygen as a ring member.

Another group of compounds which is preferred among the S group compounds, designated the T group compounds, are those compounds of the S group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and $R^3$ is selected form the group consisting of 3-indolyl-$CH_2$—, phenyl—$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

The following compounds are particularly preferred of the T Group compounds: 8a(R),1(R) diastereomer or the 8a(S),1(R) diastereomer of the compound selected from the group consisting of 2-amino-N-{1(R)-benzyloxymethyl-2-[8a-(4-fluoro-benzyl)-6-oxo-8-pyrrolidin-1-yl-3, 4,6,8a-tetrahydro-1H-pyrrolo[1,2-a]pyrazin-2-yl]-2-oxo-ethyl}-2-methyl-propionamide or 2-amino-N{1(R)-benzyloxymethyl-2-[8a-(4-fluoro-benzyl)-8-morpholin-4-yl-6-oxo-3, 4,6,8a-tetrahydro-1H-pyrrolo[1,2-a]pyrazin-2-yl]-2-oxo-ethyl}-2-methyl-propionamide.

Another group of compounds preferred among the N group compounds, designated the U group compounds, are the group compounds wherein $R^2$ is hydrogen or $(C_1-C_3)$ alkyl where the alkyl is optionally substituted with 1–3 fluoro groups;

$R^{2A}$ is hydrogen, -$(C_1-C_4)$alkyl, -$(C_0-C_2)$alkyl-$(C_1-C_6)$cycloalkyl, -$(C_0-C_2)$alkyl-$A^1$ where the alkyl groups are optionally substituted with 1–3 fluoro groups;

$A^1$ is phenyl, pyridyl or thiazolyl optionally substituted with one to two substituents, each substituent being independently selected from the group consisting of F, Cl, $CH_3$, $OCF_2H$, $OCF_3$, and $CF_3$.

Another group of compounds preferred among the U group compounds, designated the V group, are those compounds of the U group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and $R^3$ is selected form the group consisting of 3-indolyl-$CH_2$—, phenyl—$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

The following compounds are particularly preferred of the V group compounds: 8a(R),1(R) diastereomer or the 8a(S), 1(R) diastereomer of 2-amino-N-[2-(8a-benzyl-6-oxo-3,4,6, 8a-tetrahydro-1H-pyrrolo[1,2-a]pyrazin-2-yl)-1(R)-benzyloxymethyl-2-oxo-ethyl]-2-methyl-propionamide.

This invention also provides:

methods for increasing levels of endogenous growth hormone in a human or other animal which comprise administering to such human or animal a therapeutically effective amount of a compound, a salt or a prodrug of Formula I;

pharmaceutical compositions which comprise a pharmaceutically acceptable carrier and an effective amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug Formula I;

pharmaceutical compositions useful for increasing the endogenous production or release of growth hormone in a human or other animal which comprise a pharmaceutically acceptable carrier, a therapeutically effective amount of a compound, a salt or a prodrug of formula and a growth hormone secretagogue selected from the group consisting of GHRP-6, Hexarelin, GHRP-1, growth hormone releasing factor (GRF), IGF-1, IGF-2 and B-HT920 or an analog thereof;

methods for treating osteoporosis and/or frailty which comprise administering to a human or other animal in need of such treatment an amount of a compound, a salt or a prodrug of Formula I which is therapeutically effective in treating osteoporosis and/or frailty;

methods for treating diseases or conditions which may be treated by growth hormone which comprises administering to a human or other animal in need of such treatment an amount of a compound or a prodrug of Formula I which is therapeutically effective in promoting release of endogenous growth hormone.

preferred methods of the immediately foregoing methods is where the disease or condition is congestive heart failure, frailty associated with aging or obesity;

methods for accelerating bone fracture repair, attenuating protein catabolic response after a major operation, reducing cachexia and protein loss due to acute or chronic illness, accelerating wound healing, or accelerating the recovery of burn patients or patients having undergone major surgery, which method comprises administering to a mammal in need of such treatment an amount of a compound, a salt or a prodrug of Formula I which is therapeutically effective in promoting release of endogenous growth hormone.

preferred of the immediately foregoing methods is for accelerating the recovery of patients having undergone major surgery or for accelerating fracture repairs;

methods for improving muscle strength, mobility, maintenance of skin thickness, metabolic homeostasis or renal homeostasis, which method comprises administering to a human or other animal in need of such treatment an amount of a compound, a salt or a prodrug of Formula I which is therapeutically effective in promoting release of endogenous growth hormone;

methods for the treatment of osteoporosis and/or frailty which comprises administering to a human or other animal with osteoporosis and/or frailty therapeutically effective amounts of a bisphosphonate compound and a compound, a salt or a prodrug of Formula I;

methods for the treatment of osteoporosis and/or frailty wherein the bisphosphonate compound is alendronate or ibandronate;

methods for the treatment of osteoporosis and/or frailty which comprises administering to a human or other animal with osteoporosis and/or frailty therapeutically effective amounts of estrogen or Premarin® and a compound, a salt or a prodrug of Formula I and, optionally, progesterone;

methods for the treatment of osteoporosis and/or frailty which comprises administering to a human or other animal with osteoporosis and/or frailty therapeutically effective amounts of calcitonin and a compound, salt or prodrug of Formula I;

methods to increase IGF-1 levels in a human or other animal deficient in IGF-1 which comprises administering to a human or other animal with IGF-1 deficiency a compound, a salt or a prodrug of Formula I;

methods for the treatment of osteoporosis and/or frailty which comprises administering to a human or other animal with osteoporosis and/or frailty therapeutically effective amounts of an estrogen agonist or antagonist and a compound, a salt or a prodrug of Formula I;

preferred methods of the immediately foregoing method is where the estrogen agonist or antagonist is tamoxifen, droloxifene, raloxifene or idoxifene, cis-6-(4-fluorophenyl)-5-[4-(2-piperidin-1-yl-ethoxy)phenyl]-5,6,7,8-tetrahydro-naphthalene-2-ol; (−)-cis-6-phenyl-5-[4-(2-pyrrolidin-1-yl-ethoxy)phenyl]-5,6,7,8-tetrahydro-naphthalene-2-ol; cis-6-phenyl-5-[4-(2-pyrrolidin-1-yl-ethoxy)phenyl]-5,6,7,8-tetrahydro-naphthalene-2-ol; cis-1-[6'-pyrrolodinoethoxy-3'-pyridyl]-2-phenyl-6-hydroxy-1,2,3,4-tetrahydro-naphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-[4-(2-piperidin-1-yl-ethoxy)-phenyl]-5,6,7,8-tetrahydro-naphthalene-2-ol; or 1-(4'-pyrrolidinolethoxyphenyl)-2-phenyl-6-hydroxy-1,2,3,4-tetrahydro-isoquinoline.

methods for enhancing growth and improving carcass quality of an animal other than humans which comprise administering to the animal a therapeutically effective amount of a compound, a salt or a prodrug of Formula I;

methods for enhancing feed efficiency in an animal other than humans which comprises administering to the animal an therapeutically effective amount of a compound, a salt or a prodrug of Formula I.

methods for increasing milk production in a female mammal which comprises administering to the female mammal a therapeutically effective amount of a compound, a salt or a prodrug of Formula 1;

methods for increasing piglet number, increasing pregnancy rate in sows, increasing viability of piglets, increasing weight of piglets or increasing muscle fiber size in piglets which comprises administering to a sow or piglet a therapeutically effective amount of a compound, a salt or a prodrug of Formula I;

methods for increasing muscle mass, which method comprises administering to a human or other animal in need of such treatment a therapeutically effective amount of a compound, salt or a prodrug of Formula I which is therapeutically effective in promoting release of endogenous growth hormone;

methods for promoting growth in growth hormone deficient children which comprises administering to a growth hormone deficient child a compound, a salt or a prodrug of Formula I which is therapeutically effective in promoting release of endogenous growth hormone;

methods for the treatment or prevention of congestive heart failure, obesity or frailty associated with aging, which comprise administering to a human or other animal in need thereof therapeutically effective amounts of a functional somatostatin antagonist and a compound or a prodrug of Formula I;

methods wherein the functional somatostatin antagonist is an alpha-2 adrenergic agonist and the other animal is a dog, cat or a horse;

methods wherein the alpha-2 adrenergic agonist is clonidine, xylazine, detomidine or medetomidine;

methods for treating insulin resistance in a mammal, which comprise administering to the mammal a therapeutically effective amount of a compound, a salt or prodrug of Formula I; and preferred methods of the immediately foregoing methods is where the condition associated with insulin resistance is type 1 diabetes, type II diabetes, hyperglycemia, imparied glucose intolerance or an insulin resistant syndrome or where the condition associated with insulin resistance is associated with obesity or old age.

The instant compounds promote the release of growth hormone which is stable under various physiological conditions and may be administered parenterally, nasally or by the oral route.

The present invention includes the compounds of the present invention, the pharmaceutically acceptable salts or prodrug thereof, wherein one or more hydrogen carbon or other atoms are replaced by istopes thereof. Such compounds may be useful as research and diagnostic tools in metabolism pharmacokinetic studies and in binding assays.

DETAILED DESCRIPTION OF THE INVENTION

In general the compounds of Formula I can be made by processes known in the chemical arts. Certain processes for the manufacture of Formula I compounds are provided as further features of the invention and are illustrated by the following reaction schemes.

In the above structural formulae and throughout the instant application, the following terms have the indicated meanings unless expressly stated otherwise:

The alkyl groups are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, ethynyl, propenyl, butadienyl, hexenyl and the like.

When the definition CO-alkyl occurs in the definition, it means a single covalent bond.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, 2-propynyloxy, isobutenyloxy, hexenyloxy and the like.

The term "halogen" or "halo" is intended to include the halogen atoms fluorine, chlorine, bromine and iodine.

The term "halogenated alkyl" is intended to include an alkyl group as defined herein above substituted by one or more halogen atoms as defined herein above.

The term "halogenated cycloalkyl" is intended to include a cycloalkyl group substituted by one or more halogen atoms as defined herein above.

The term "aryl" is intended to include phenyl and naphthyl and aromatic 5- and 6-membered rings with 1 to 4 heteroatoms or fused 5- and/or 6-membered bicyclic rings with 1 to 4 heteroatoms of nitrogen, sulfur or oxygen. Examples of such heterocyclic aromatic rings are pyridine, thiophene (also known as thienyl), furan, benzothiophene, tetrazole, indole, N-methylindole, dihydroindole, indazole, N-formylindole, benzimidazole, thiazole, pyrimidine, and thiadiazole.

The expression "prodrug" refers to compounds that are drug precursors which following administration, release the drug in vivo via some chemical or physiological process (e.g., a prodrug on being brought to the physiological pH is converted to the desired drug form). Exemplary prodrugs upon cleavage release the corresponding free acid, and such hydrolyzable ester-forming residues of the compounds of this invention include but are not limited to carboxylic acid substituents (e.g., when $R^1$ is $-(CH_2)_qC(O)OX^6$ where $X^6$ is hydrogen, or when $R^2$ or $A^1$ contains carboxylic acid) wherein the free hydrogen is replaced by $(C_1–C_4)$alkyl, $(C_2–C_{12})$alkanoyloxymethyl, $(C_4–C_9)$1-(alkanoyloxy)ethyl, 1-methyl-1(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1–C_2)$alkylamino$(C_2–C_3)$alkyl (such as b-dimethylaminoethyl), carbamoyl-$(C_1–C_2)$alkyl, N,N-di$(C_1–C_2)$-alkylcarbamoyl-$(C_1–C_2)$alkyl and piperidino-, pyrrolidino- or morpholino$(C_2–C_3)$alkyl.

Other exemplary prodrugs release an alcohol of Formula I wherein the free hydrogen of the hydroxyl substituent (e.g., when $R^1$ contains hydroxyl) is replaced by $(C_1–C_6)$alkanoyloxymethyl, 1-(($C_1–C_6$)alkanoyloxy)ethyl, 1-methyl-1-(($C_1–C_6$)alka-noyloxy)ethyl, $(C_1–C_6)$alkoxycarbonyloxymethyl, N-$(C_1–C_6)$alkoxycarbonylamino-methyl, succinoyl, $(C_1–C_6)$alkanoyl, a-amino$(C_1–C_4)$alkanoyl, arylacetyl and a-aminoacyl, or a-aminoacyl-a-aminoacyl wherein said a-aminoacyl moieties are independently any of the naturally occurring L-amino acids found in proteins, $-P(O)(OH)_2$, $-P(O)(O(C_1–C_6)$alkyl$)_2$ or glycosyl (the radical resulting from detachment of the hydroxyl of the hemiacetal of a carbohydrate).

Prodrugs of this invention where a carboxyl group in a carboxylic acid of Formula I is replaced by an ester may be prepared by combining the carboxylic acid with the appropriate alkyl halide in the presence of a base such as potassium carbonate in an inert solvent such as DMF at a temperature of about 0° C. to 100° C. for about 1 to about 24 hours. Alternatively, the acid is combined with the appropriate alcohol as solvent in the presence of a catalytic amount of acid such as concentrated sulfuric acid at a temperature of about 20° C. to 120° C., preferably at reflux, for about 1 hour to about 24 hours. Another method is the reaction of the acid in an inert solvent such as THF, with concomitant removal of the water being produced by physical (e.g., Dean Stark trap) or chemical (e.g., molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as DMF at a temperature of about 0° C. to 100° C. for about 1 to about 24 hours. Alkanoylaminomethyl ethers may be obtained by reaction of the alcohol with a bis-(alkanoylamino)$_m$ethane in the presence of a catalytic amount of acid in an inert solvent such as THF, according to a method described in U.S. Pat. No. 4,997,984. Alternatively, these compounds may be prepared by the methods described by Hoffman et al. in J. Org. Chem. 1994, 59, p. 3530.

Certain of the above defined terms may occur more than once in the above formula and upon such occurrence each term shall be defined independently of the other.

The compounds of Formula I above contains chiral centers and therefore may exist in different enantiomeric dorms. This invention relates to all optical isomers at all other stereoisomers (e.g. diasteriomers) of compounds of Formula I and mixtures thereof.

The compounds of the instant invention all have at least one asymmetric center as noted by the asterisk in the structural Formula I. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the instant invention. In the case of the asymmetric center represented by the asterisk, it has been found that the absolute stereochemistry of the more active and thus more preferred isomer is shown in Formula IA. This preferred absolute configuration also applies to Formula I.

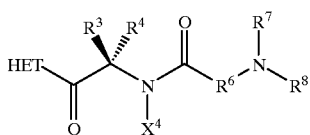

IA

With the $R^4$ substituent as hydrogen, the spatial configuration of the asymmetric center corresponds to that in a D-amino acid. In most cases this is also designated an R-configuration although this will vary according to the values of $R^3$ and $R^4$ used in making R- or S-stereochemical assignments.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts are formed by taking about 1 equivalent of a compound of Formula I and contacting it with about 1 equivalent of the appropriate corresponding acid of the salt which is desired. Work-up and isolation of the resulting salt is well-known to those of ordinary skill in the art.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release.

The compounds of Formula I can be administered to animals, including humans, to release growth hormone in vivo. The compounds are useful for treating symptoms related to GH deficiency; stimulating pre- and post-natal growth or enhancing feed efficiency and improving carcass quality of animals raised for meat production; increasing milk production in dairy cattle; improving estrous synchronization in livestock such as swine, beef and dairy cattle; improving bone or wound healing and improving vital organ function in animals. The compounds of the present invention, by inducing endogenous GH secretion, will alter body composition and modify other GH-dependent metabolic, immunologic or developmental processes. For example, the compounds of the present invention can be given to chickens, turkeys, livestock animals (such as sheep, pigs, horses, cattle, etc.) and companion animals (e.g., dogs). These compounds may also have utility in aquaculture to accelerate growth and improve the percent lean meat. In addition, these compounds can be administered to humans in vivo as a diagnostic tool to directly determine whether the pituitary is capable of releasing growth hormone. For example, the compounds of Formula I or a pharmaceutically acceptable salt or prodrug thereof can be administered in vivo to children and serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I or a pharmaceutically acceptable salt or prodrug thereof in association with a pharmaceutically acceptable carrier. Optionally, the pharmaceutical compositions can further comprise an anabolic agent in addition to at least one of the compounds of Formula I or a pharmaceutically acceptable salt or prodrug thereof, or another compound which exhibits a different activity, e.g., an antibiotic or coccidiostat (e.g., monensin) growth promotant or an agent to treat osteoporosis or with other pharmaceutically active materials wherein the combination enhances efficacy and minimizes side effects.

Growth promoting and anabolic agents include, but are not limited to, TRH, PTH, diethylstilbesterol, estrogens, 13-agonists, theophylline, anabolic steroids, enkephalins, E series prostaglandins, compounds disclosed in U.S. Pat. No. 3,239,345, the disclosure of which is hereby incorporated by reference, e.g., zeranol; compounds disclosed in U.S. Pat. No. 4,036,979, the disclosure of which is hereby incorporated by reference, e.g., sulbenox; and peptides disclosed in U.S. Pat. No. 4,411,890, the disclosure of which is hereby incorporated by reference.

The growth hormone secretagogues of this invention in combination with other growth hormone secretagogues such as the growth hormone releasing peptides GHRP-6 and GHRP-1 as described in U.S. Pat. No. 4,411,890, the disclosure of which is hereby incorporated by reference, and publications WO 89/07110, WO 89/07111 and B-HT920 as well as hexarelin and the newly discovered GHRP-2 as described in WO 93/04081 or growth hormone releasing hormone (GHRH, also designated GRF) and its analogs or growth hormone and its analogs or somatomedins including IGF-1 and IGF-2 or alpha-2-adrenergic agonists such as clonidine, xylazine, detomidine and medetomidine or serotonin 5HTID agonists such as sumitriptan or agents which inhibit somatostatin or its release such as physostigmine and pyridostigmine, are useful for increasing the endogenous levels of GH in mammals. The combination of a GH secretagogue of this invention with GRF results in synergistic increases of endogenous growth hormone.

As is well known to those skilled in the art, the known and potential uses of growth hormone are varied and multitudinous [See "Human Growth Hormone", Strobel and Thomas, Pharmacological Reviews, 46, pg. 1–34 (1994); T. Rosen et al., Horm Res, 1995; 43: pp. 93–99; M. Degerblad et al., European Journal of Endocrinology, 1995, 133: pp.180–188; J. O. Jorgensen, European Journal of Endocrinology, 1994, 130: pp. 224–228; K. C. Copeland et al., Journal of Clinical Endocrinology and Metabolism, Vol. 78 No. 5, pp. 1040–1047; J. A. Aloi et al., Journal of Clinical Endocrinology and Metabolism, Vol. 79 No. 4, pp. 943–949; F. Cordido et al., Metab. Clin. Exp., (1995), 44(6), pp. 745–748; K. M. Fairhall et al., J. Endocrinol., (1995), 145(3), pp. 417–426; R. M. Frieboes et al., Neuroendocrinology, (1995), 61(5), pp. 584–589; and M. Llovera et al., lnt. J. Cancer, (1995), 61(1), pp. 138–141]. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans or companion animals especially dogs, cats, camels and horses; treating growth hormone deficient adult humans or other animals especially dogs, cats, camels and horses; preventing catabolic side effects of glucocorticoids, treating osteoporosis, stimulating the immune system, accelerating wound healing, accelerating bone fracture repair, treating growth retardation, treating congestive heart failure as disclosed in PCT publications WO 95/28173 and WO 95/28174 (an example of a method for assaying growth hormone secretagogues for efficacy in treating congestive heart failure is disclosed in R. Yang et al., Circulation, Vol. 92, No. 2, p.262, 1995), treating acute or chronic renal failure or insufficiency; treating physiological short stature including growth hormone deficient children, treating short stature associated with chronic illness, treating obesity, treating growth retardation associated with Prader-Willi syndrome and Turner's syndrome; accelerating the recovery and reducing hospitalization of burn patients or following major surgery such as gastrointestinal surgery; treating intrauterine growth retardation, skeletal dysplasia, hypercortisonism and Cushings syndrome; replacing growth hormone in stressed patients; treating osteochondrodysplasias, Noonans syndrome, sleep disorders, Alzheimer's disease, delayed wound healing, and psychosocial deprivation; treating pulmonary dysfunction and ventilator dependency; attenuating protein catabolic response after a major operation; treating malabsorption syndromes, reducing cachexia and protein loss due to chronic illness such as cancer or AIDS; accelerating weight gain and protein accretion in patients on TPN (total parenteral nutrition); treating hyperinsulinemia including nesidioblastosis; adjuvant treatment for ovulation induction and to prevent and treat gastric and duodenal ulcers; stimulating thymic development and preventing age-related decline of thymic function; adjunctive therapy for patients on chronic hemodialysis; treating immunosuppressed patients and enhancing antibody response following vaccination; improving muscle strength, increasing muscle mass, mobility, maintenance of skin thickness, metabolic homeostasis, renal hemeostasis in the frail elderly; stimulating osteoblasts, bone remodeling, and cartilage growth; treating neurological diseases such as peripheral and drug induced neuropathy, Guillian-Barre Syndrome, amyotrophic lateral sclerosis, multiple sclerosis, cerebrovascular accidents and demyelinating diseases; and stimulating wool growth in sheep.

Uses of GH in farm animals raised for meat production such as chickens, turkeys, sheep, pigs and cattle include stimulation of pre- and post- natal growth, enhanced feed efficiency in animals raised for meat production, improved carcass quality (increased muscle to fat ratio) (Campbell, R. G. et al., (1989), J. Anim. Sci. 67, 1265; Dave, D. J., Bane, D. P., (1990), The Compendium Food Anual, Vol. 12(1), 117; Holden, P. J., (1990), Agri-Practice, 11(3), 25; Claus, R., Weiber, U., (1994), Livestock Production Science, 37, 245; Roeder, R. et al., (1994), Growth Regulation, 4, 101); increased milk production in dairy cattle (McBride, B. W. et al., (1988), Research and Development in Agriculture 5(1), 1; McDowell, G. H. et al., (1988), Aust. J. Biol. Sci., 41, 279); improved body composition; modification of other GH-dependent metabolic (Claus, R. and Weiber, U., (1994), Livestock Production Science, 37, 245) and immunologic functions such as enhancing antibody response following vaccination or improved developmental processes; and may have utility in aquaculture to accelerate growth and improve the protein-to-fat ratio in fish.

Preferred uses in companion animals include stimulating endogenous growth hormone release in companion animals such as dogs, cats and horses; treating disorders of aging (Detenbeck, L. C., Jowsey, J., Clinical Orthopedics and Related Research, July–August 1969, No. 65, pp. 76–80); stimulating thymic development and preventing age-related decline of thymic function (Goff, B. L. et al., Clinical and Experimental Immunology, 1987, 68:3, pp. 580–587; Morrison, W. B. et al., Am. J. Vet. Res., Jan. 1990, 51:1, pp. 65–70; Roth, J. A. et al., Am. J. Vet. Res., 1984, Vol. 45, pp. 1151–1155); preventing age-related decline of thymic function; preventing age-related decline in cognition; accelerating wound healing (Jacks, T. et al., Vet. Surg. 1996, 25, (5), 430); accelerating bone fracture repair (Pandey, S. K., Udupa, K. N., Indian J. Vet. Surg. 1 (2): 73–78, July 1980); stimulating osteoblasts, bone remodelling and cartilage growth (Harris, W. H. et al., Calc. Tiss. Res., 10, 1972, pp. 1–13; Heaney, R. P. et al., Calc. Tiss. Res. 10, 1972, pp. 14–22; Mankin. H. J. et al., J. of Bone and Joint Surgery, Vol. 60-A, #8, December 1978, pp. 1071–1075); attenuating protein catabolic response after major surgery, accelerating recovery from burn injuries and major surgeries such as gastrointestinal surgery; stimulating the immune system and enhancing antibody response following vaccination; treating congestive heart failure, treating acute or chronic renal failure or insufficiency, treating obesity; treating growth retardation, skeletal dysplasia and osteochondrodysplasias; preventing catabolic side effects of glucocorticoids; treating Cushing's syndrome; treating malabsorption syndromes, reducing cachexia and protein loss due to chronic illness such as cancer; accelerating weight gain and protein accretion in animals receiving total parenteral nutrition; providing adjuvant treatment for ovulation induction and to prevent gastrointestinal ulcers; improving muscle mass, strength and mobility; maintenance of skin thickness, and improving vital organ function and metabolic homeostasis.

The growth hormone secretagogues of this invention, compounds of Formula I, or a pharmaceutically acceptable salt or prodrug thereof in combination with an alpha-2 adrenergic agonist are useful in promoting GH secretion in humans and other animals (See Cella, S. G. et al., Acta Endocrinologica (Copenh.) 1989, 121, pp. 177–184). As such, a combination of a compound of Formula I or a pharmaceutically acceptable salt or prodrug thereof and an alpha-2 adrenergic agonist is useful in the treatment or prevention of frailty associated with aging, congestive heart failure and obesity which comprises administering to a human or another animal, especially dogs, cats and horses, in need of such treatment a combination of an alpha-2 adrenergic agonist and a compound of Formula I or a pharmaceutically acceptable salt or prodrug thereof, defined above. Preferred alpha-2 adrenergic agonists include clonidine, which is disclosed in U.S. Pat. No. 3,202,660 the disclosure of which is hereby incorporated by reference, xylazine, which is disclosed in U.S. Pat. No. 3,235,550 the disclosure of which is hereby incorporated by reference and medetomidine, which is disclosed in U.S. Pat. No. 4,544,664 the disclosure of which is hereby incorporated by reference. In another aspect, this invention provides methods for accelerating bone fracture repair and wound healing, attenuating protein catabolic response after a major operation, and reducing cachexia and protein loss due to chronic illness, which comprise administering to a human or another animal, especially dogs, cats and horses in need of such treatment a combination of an alpha-2 adrenergic agonist such as clonidine, xylazine or medetomidine and a compound of Formula I or a pharmaceutically acceptable salt or prodrug thereof. It has been shown that alpha-2 adrenergic agonists cause release of endogenous growth hormone in human and canine subjects (Celia et al., Life Sciences (1984), 34:447–454; Hampshire J, Altszuler N., American Journal of Veterinary Research (1981), 42:6, 1073–1076; Valcavi et al., Clinical Endocrinology (1988), 29:309–316; Morrison et al., American Journal of Veterinary Research (1990), 51:1, 65–70;), and that the co-administration of an alpha-2 adrenergic agonist with growth hormone-releasing factor restores defective growth hormone secretion in aged dogs (Arce et al., Brain Research (1990), 537:359–362; Celia et. al., Neuroendocrinology (1993), 57:432–438).

This invention also relates to a method of treating insulin resistant conditions such as Non-Insulin Dependent Diabetes Mellitus (NIDDM) and reduced glycemic control associated with obesity and aging in a mammal in need thereof which comprises administering to said mammal an effective amount of a compound of the Formula I or a pharmaceutically acceptable salt or prodrug thereof.

This invention is directed to the use of growth hormone secretagogues specifically growth hormone releasing peptides (GHRP) or GHRP mimetics of Formula I or a pharmaceutically acceptable salt or prodrug thereof to improve glycemic control. Agents that increase growth hormone (GH) levels would not be expected to have this effect since it is widely recognized that GH is diabetogenic in animals and in humans. In acromegalics, glucose utilization and suppression of hepatic glucose production are impaired (see Hansen, I., et al., Am J Physiol, 250:E269 (1986)). In this disease of GH excess, impaired glucose handling and hyperinsulinemia have been reversed by pituitary surgery or chemotherapy which reduced GH levels (see Levin S. R., et al., Am J Med, 57:526 (1974), Feek, C. M., et al., J Clin Endocrinol 22:532 (1981)). Furthermore, administration of GH to older subjects caused hyperglycemia, glucose intolerance and hyperinsulinemia in numerous studies (see Aloia, J. F., et al., J Clin Endocrinol Metab, 43:992 (1976); Binnerts et al., J Clin Endocrinol Metab, 67:1312 (1988); Marcus, R., et al., J Clin Endocrinol Metab, 70:519 (1990)). Therefore, GH therapy is contra-indicated for individuals with diabetes or those at risk for diabetes.

It will be known to those skilled in the art that there are numerous compounds now being used in an effort to treat the diseases or therapeutic indications enumerated above. Combinations of these therapeutic agents, some of which have also been mentioned above, with growth promotant, exhibit anabolic and desirable properties of these various therapeutic agents. In these combinations, the therapeutic agents and the growth hormone secretagogues of this invention may be independently and sequentially administered in any order or co-administered in dose ranges from one one-hundredth to one times the dose levels which are effective when these compounds and secretagogues are used singly. Combined therapy to inhibit bone resorption, prevent osteoporosis, reduce skeletal fracture, enhance the healing of bone fractures, stimulate bone formation and increase bone mineral density can be effectuated by combinations of bisphosphonates and the growth hormone secretagogues of this invention. See PCT publication WO 95/11029 for a discussion of combination therapy using bisphosphonates and GH secretagogues. The use of bisphosphonates for these utilities has been reviewed, for example, by Hamdy, N. A. T., Role of Bisphosphonates in Metabolic Bone Diseases, Trends in Endocrinol. Metab., 1993, 4, pages 19–25. Bisphosphonates with these utilities include but are not limited to alendronate, tiludronate, dimethyl-APD, risedronate, etidronate, YM-175, clodronate, pamidronate, and BM-210995 (ibandronate). According to their potency, oral daily dosage levels of the bisphosphonate of between 0.1 mg/kg and 5 g/kg of body weight and daily dosage levels of the growth hormone secretagogues of this invention of between 0.01 mg/kg to 20 mg/kg of body weight are administered to patients to obtain effective treatment of osteoporosis.

The compounds of this invention may be combined with a mammalian estrogen agonist/antagonist. Any estrogen agonist/antagonist may be used as the second compound of this invention. The term estrogen agonist/antagonist refers to compounds which bind with the estrogen receptor, inhibit bone turnover and prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art according to standard assays including estrogen receptor binding assays, standard bone histomorphometric and densitometer methods (see Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below, however, other estrogen agonists/antagonists will be known to those skilled in the art. A preferred estrogen agonist/antagonist is droloxifene: (phenol, 3-[1-[4[2-(dimethylamino)ethoxy]-phenyl]-2-phenyl-1-butenyl]-, (E)-) and associated compounds which are disclosed in U.S. Pat. No. 5,047,431, the disclosure of which is hereby incorporated by reference.

Another preferred estrogen agonist/antagonist is tamoxifen: (ethanamine,2-[4-(1,2-diphenyl-1-butenyl)phenoxy]-N,N-dimethyl, (Z)-2,2-hydroxy-1,2,3-propanetricarboxylate (1:1)) and associated compounds which are disclosed in U.S. Pat. No. 4,536,516, the disclosure of which is hereby incorporated by reference. Another related compound is 4-hydroxy tamoxifen which is disclosed in U.S. Pat. No. 4,623,660, the disclosure of which is hereby incorporated by reference.

Another preferred estrogen agonist/antagonist is raloxifene: (methanone, [6-hydroxy-2-(4-hydroxyphenyl)benzo[b]thien-3-yl][4-[2-(1-piperidinyl)ethoxy]phenyl]-, hydrochloride) and associated compounds which are disclosed in U.S. Pat. No. 4,418,068, the disclosure of which is hereby incorporated by reference.

Another preferred estrogen agonist/antagonist is idoxifene: Pyrrolidine, 1-[-[4-[[1-(4-iodophenyl)-2-phenyl-1-Butenyl]phenoxy]ethyl] and associated compounds which are disclosed in U.S. Pat. No. 4,839,155, the disclosure of which is hereby incorporated by reference.

Other preferred estrogen agonist/antagonists include compounds as described in commonly assigned U.S. Pat. No. 5,552,412 the disclosure of which is hereby incorporated by reference. Especially preferred compounds which are described therein are:

cis-6-(4-fluoro-phenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol; and 1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814, the disclosure of which is hereby incorporated by reference. U.S. Pat. No. 4,133,814 discloses derivatives of 2-phenyl-3-aroyl-benzothiophene and 2-phenyl-3-aroylbenzothiophene-1-oxide.

The following paragraphs provide preferred dosage ranges for various anti-resorptive agents.

The amount of the anti-resorptive agent to be used is determined by its activity as a bone loss inhibiting agent. This activity is determined by means of an individual compound's pharmacokinetics and its minimal maximal effective dose in inhibition of bone loss using a protocol such as those referenced above.

In general a therapeutically effective dosage for the activities of this invention, for example the treatment of osteoporosis, for the estrogen agonists/antagonists (when used in combination with a compound of Formula I or a pharmaceutically acceptable salt or prodrug thereof of this invention) is in the range of 0.01 to 200 mg/kg/day, preferably 0.5 to 100 mg/kg/day.

In particular, an effective dosage for droloxifene is in the range of 0.1 to 40 mg/kg/day, preferably 0.1 to 5 mg/kg/day.

In particular, an effective dosage for raloxifene is in the range of 0.1 to 100 mg/kg/day, preferably 0.1 to 10 mg/kg/day.

In particular, an effective dosage for tamoxifen is in the range of 0.1 to 100 mg/kg/day, preferably 0.1 to 5 mg/kg/day.

In particular, an effective dosage for cis-6-(4-fluoro-phenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol; or 1-(4'-pyrrolidinolethoxyphenyl)-2-phenyl-6-hydroxy-1,2,3,4-tetrahydroisoquinoline is in the range of 0.0001 to 100 mg/kg/day, preferably 0.001 to 10 mg/kg/day.

In particular, an effective dosage for 4-hydroxy tamoxifen is in the range of 0.0001 to 100 mg/kg/day, preferably 0.001 to 10 mg/kg/day.

The term "treating" as used herein, unless otherwise indicated, means reversing, alleviating, inhibiting the progress of, or preventing the disorder or condition to which such term applies on one or more symptoms of such disorder or condition. The term "treatment" as used herein, refers to the act of treating, as "treating" is defined immediately above.

Assay for Stimulation of GH Release from Rat Pituicytes

Compounds that have the ability to stimulate GH secretion from cultured rat pituitary cells are identified using the following protocol. This test is also useful for comparison to standards to determine dosage levels. Cells are isolated from pituitaries of 6-week old male Wistar rats. Following decapitation, the anterior pituitary lobes are removed into cold, sterile Hank's balanced salt solution without calcium or magnesium (HBSS). Tissues are finely minced, then subjected to two cycles of mechanically assisted enzymatic dispersion using 10 U/mL bacterial protease (EC 3.4.24.4, Sigma P-6141, St. Louis, Mo.) in HBSS. The tissue-enzyme mixture is stirred in a spinner flask at 30 rpm in a 5% $CO_2$ atmosphere at about 37° C. for about 30 min., with manual trituration after about 15 min. and about 30 min. using a 10-mL pipet. This mixture is centrifuged at 200×g for about 5 min. Horse serum (35% final concentration) is added to the supernatant to neutralize excess protease. The pellet is resuspended in fresh protease (10 U/mL), stirred for about 30 min. more under the previous conditions, and manually triturated, ultimately through a 23-gauge needle. Again, horse serum (35% final concentration) is added, then the cells from both digests are combined, pelleted (200×g for about 15 min.), resuspended in culture medium (Dulbecco's Modified Eagle Medium (D-MEM) supplemented with 4.5 g/L glucose, 10% horse serum, 2.5% fetal bovine serum, 1% non-essential amino acids, 100 U/mL nystatin and 50 mg/mL gentamycin sulfate, Gibco, Grand Island, N.Y.) and counted. Cells are plated at 6.0–6.5×10$^4$ cells per cm$^2$ in 48-well Costar™ (Cambridge, Mass.) dishes and cultured for 3–4 days in culture medium.

Just prior to GH secretion assay, culture wells are rinsed twice with release medium, then equilibrated for about 30 minutes in release medium (D-MEM buffered with 25 mM Hepes, pH 7.4 and containing 0.5% bovine serum albumin at 37° C.). Test compounds are dissolved in DMSO, then diluted into pre-warmed release medium. Assays are run in quadruplicate. The assay is initiated by adding 0.5 mL of release medium (with vehicle or test compound) to each culture well. Incubation is carried out at about 37° C. for about 15 minutes, then terminated by removal of the release medium, which is centrifuged at 2000×g for about 15 minutes to remove cellular material. Rat growth hormone concentrations in the supernatants are determined by a standard radioimmunoassay protocol described below.

Measurement of Rat Growth Hormone

Rat growth hormone concentrations were determined by double antibody radioimmunoassay using a rat growth hormone reference preparation (NIDDK-rGH-RP-2) and rat growth hormone antiserum raised in monkey (NIDDK-antirGH-S-5) obtained from Dr. A. Parlow (Harbor-UCLA Medical Center, Torrence, Calif.). Additional rat growth hormone (1.5 U/mg, #G2414, Scripps Labs, San Diego, Calif.) is iodinated to a specific activity of approximately 30 $\mu$Ci/$\mu$g by the chloramine T method for use as tracer. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation. This assay has a working range of 0.08–2.5 $\mu$g rat growth hormone per tube above basal levels.

Assay for Exogenously-Stimulated Growth Hormone Release in the Rat after Intravenous Administration of Test Compounds Twenty-one day old female Sprague-Dawley rats (Charles River Laboratory, Wilmington, Mass.) are allowed to acclimate to local vivarium conditions (24° C., 12 hr light, 12 hr dark cycle) for approximately 1 week before compound testing. All rats are allowed access to water and a pelleted commercial diet (Agway Country Food, Syracuse N.Y.) ad libitum. The experiments are conducted in accordance with the NIH Guide for the Care and Use of Laboratory Animals.

On the day of the experiment, test compounds are dissolved in vehicle containing 1% ethanol, 1 mM acetic acid and 0.1% bovine serum albumin in saline. Each test is conducted in three rats. Rats are weighed and anesthetized via intraperitoneal injection of sodium pentobarbital (Nembutol®, 50 mg/kg body weight). Fourteen minutes after anesthetic administration, a blood sample is taken by nicking the tip of the tail and allowing the blood to drip into a microcentrifuge tube (baseline blood sample, approximately 100 $\mu$l). Fifteen minutes after anesthetic administration, test compound is delivered by intravenous injection into the tail vein, with a total injection volume of 1 mL/kg body weight. Additional blood samples are taken from the tail at 5, 10 and 15 minutes after compound administration. Blood samples are kept on ice until serum separation by centrifugation (1430×g for 10 minutes at 10° C.). Serum is stored at −80° C. until serum growth hormone determination by radioimmunoassay as described above.

Assessment of Exogenously-Stimulated Growth Hormone Release in the Dog after Oral Administration On the day of dosing, the test compound is weighed out for the appropriate dose and dissolved in water. Doses are delivered at a volume of 0.5–3 mL/kg by gavage to 2–4 dogs for each dosing regimen. Blood samples (5 mL) are collected from the jugular vein by direct vena puncture pre-dose and at 0.17, 0.33, 0.5, 0.75, 1, 2, 4, 6, 8 and 24 hours post dose using 5 mL vacutainers containing lithium heparin. The prepared plasma is stored at −20° C. until analysis.

Measurement of Canine Growth Hormone

Canine growth hormone concentrations are determined by a standard radioimmunoassay protocol using canine growth hormone (antigen for iodination and reference preparation AFP-1983B) and canine growth hormone antiserum raised in monkey (AFP-21452578) obtained from Dr. A. Parlow (Harbor-UCLA Medical Center, Torrence, Calif.). Tracer is produced by chloramine T-iodination of canine growth hormone to a specific activity of 20–40 $\mu$Ci/$\mu$g. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation. This assay has a working range of 0.08–2.5 $\mu$g canine GH/tube.

Assessment of Canine Growth Hormone and Insulin-Like Growth Factor-1 Levels in the Dog After Chronic Oral Administration The dogs receive test compound daily for either 7 or 14 days. Each day of dosing, the test compound is weighed out for the appropriate dose and dissolved in water. Doses are delivered at a volume of 0.5–3 ml/kg by gavage to 5 dogs for each dosing regimen. Blood samples are collected at days 0, 3, 7, 10 and 14. Blood samples (5 ml) are obtained by direct venipuncture of the jugular vein at pre-dose, 0.17, 0.33, 0.5, 0.754, 1, 2, 3, 6, 8, 12 and 24 hours post administration on days 0, 7 and 14 using 5 ml vacutainers containing lithium heparin. In addition, blood is drawn pre-dose and 8 hours on days 3 and 10. The prepared plasma is stored at −20° C. until analysis.

Plasma insulin is determined by radioimmunoassay using a kit from Binax Corp. (Portland, Maine). The interassay coefficient of variation is $\leq$10%. Plasma triglycerides, total cholesterol, glucose and lactate levels are measured using Abbott VP™ and VP Super System® Autoanalyzer (Abbott Laboratories, Irving, Tex.), using the A-Gent™ Triglycerides, Cholesterol and Glucose Test reagent systems, and a lactate kit from Sigma, respectively. The plasma insulin, triglycerides, total cholesterol and lactate lowering activity of a growth hormone releasing peptide (GHRP) or GHRP mimetic such as a compound of Formula I, are determined by statistical analysis (unpaired t-test) with the vehicle-treated control group.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated with pharmaceutically acceptable carriers to provide dosage forms appropriate for each route of administration.

Solid dosage forms for oral administration include capsules, tablets, pills, powders and granules and for companion animals the solid dosage forms include an admixture with food and chewable forms. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings. In the case of chewable forms, the dosage form may comprise flavoring agents and perfuming agents.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to humans and other animals, e.g., mammals, to obtain effective release of growth hormone.

A preferred dosage range in humans is 0.01 to 5.0 mg/kg of body weight daily which can be administered as a single dose or divided into multiple doses.

A preferred dosage range in animals other than humans is 0.01 to 10.0 mg/kg of body weight daily which can be administered as a single dose or divided into multiple doses. A more preferred dosage range in animals other than humans is 0.1 to 5 mg/kg of body weight daily which can be administered as a single dose or divided into multiple doses.

Throughout this disclosure the following abbreviations are used with the following meanings:
BOC t-Butyloxycarbonyl
Bz Benzyl
BOP Benzotriazol-1-yloxy tris(dimethylamino) phosphonium hexafluorophosphate
CBZ Benzyloxycarbonyl
CDI N,N'-Carbonyldiimidazole
DCC Dicyclohexylcarbodiimide
DEC 1,2-Diethylaminoethyl chloride hydrochloride
DMAP 4-Dimethylaminopyridine
DMF Dimethylformamide
DPPA Diphenylphosphoryl azide
EDC 1-(3-Dimethylaminopropyl)-3-ethylcarbodiimide hydrochloride
EtOAc Ethyl acetate
Hex Hexane
HOAT 1-Hydroxy-7-azabenzotriazole
HOBT Hydroxybenzotriazole hydrate
HPLC High pressure liquid chromatography
Hz Hertz
KHMDS Potassium Bis(trimethylsilyl)amide
LHMDS Lithium Bis(trimethylsilyl)amide
MHz Megahertz
MS Mass Spectrum
NaHMDS Sodium Bis(trimethylsilyl)amide
NMR Nuclear Magnetic Resonance
PPAA 1-Propanephosphonic acid cyclic anhydride
PTH Parathyroid hormone
TFA Trifluoroacetic acid
THF Tetrahydrofuran
TLC Thin layer chromatography
TRH Thyrotropin releasing hormone The preparation of the compounds of Formula I of the present invention can be carried out in sequential or convergent synthetic routes. Syntheses detailing the preparation of the compounds of Formula I in a sequential manner are presented in the following reaction schemes.

Many protected amino acid derivatives are commercially available, where the protecting groups, Prt, Prt' or Prt", are, for example, BOC, CBZ, FMOC, benzyl or ethoxycarbonyl groups. Other protected amino acid derivatives can be prepared by literature methods well-known to one skilled in the art. Some substituted piperazines and piperidines are commercially available, and many other piperazines and 4-substituted piperidines are known in the literature. Various heterocyclic substituted piperidines and piperazines can be prepared following literature methods using derivatized heterocyclic intermediates. Alternatively, the heterocyclic rings of such compounds can be derivatized by standard means, such as coupling with CDI, hydrogenation of aromatic heterocycles, etc. as is well-known to those skilled in the art.

Many of the schemes illustrated below describe compounds which contain protecting groups Prt, Prt' or Prt", which can be any suitable protecting group known to those skilled in the art. Benzyloxycarbonyl groups can be removed by a number of methods including, catalytic hydrogenation with hydrogen in the presence of a palladium or platinum catalyst in a protic solvent such as methanol. Preferred catalysts are palladium hydroxide on carbon or palladium on carbon. Hydrogen pressures from 1–1000 psi can be employed; pressures from 10 to 70 psi are preferred. Alternatively, the benzyloxycarbonyl group can be removed by transfer hydrogenation.

Removal of BOC protecting groups can be carried out using a strong acid such as trifluoroacetic acid or hydrochloric acid with or without the presence of a cosolvent such as dichloromethane or methanol at a temperature of about −30° to 70° C., preferably about −5° to about 35° C.

Benzyl groups on amines can be removed by a number of methods including catalytic hydrogenation with hydrogen in the presence of a palladium catalyst in a protic solvent such as methanol. Hydrogen pressures from 1–1000 psi can be employed; pressures from 10 to 70 psi are preferred. The addition and removal of these and other protecting groups are discussed in detail by T. Greene in Protective Groups in Organic Synthesis, John Wiley & Sons, New York, 1981.

The variables shown in the following schemes are as described for compounds of Formula I, above, unless otherwise indicated.

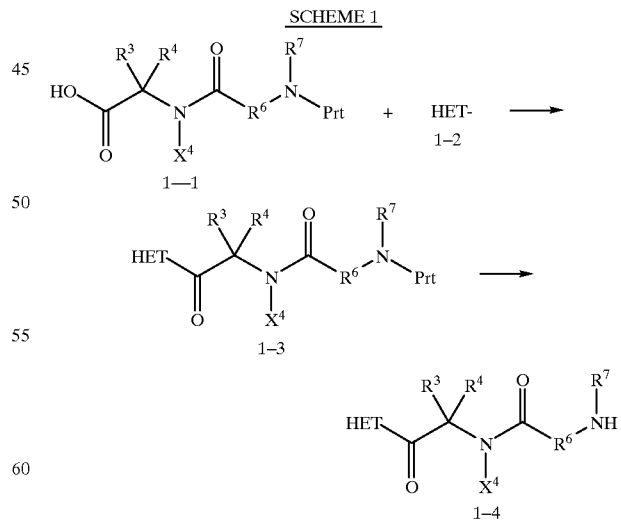

As illustrated in Scheme 1, coupling of a heterocyclic amine (HET at the NH) of formula 1-2, as defined for Formula I, with a protected amino acid of formula 1-1, where Prt is a suitable protecting group, is conveniently carried out in an inert solvent such as dichloromethane or DMF by a coupling reagent such as EDC, DCC or DEC in the presence of HOBT or HOAT. In the case where amine 1-2 is present as the hydrochloride salt, it is preferable to add one equivalent of a suitable base such as triethylamine to the reaction mixture. Alternatively, the coupling can be effected with a coupling reagent such as BOP in an inert solvent such as methanol or with PPM in a solvent like ethyl acetate. Such coupling reactions are generally conducted at temperatures of about −30° to about 80° C., preferably 0° to about 25° C. For a discussion of other conditions used for coupling peptides see Houben-Weyl, Vol. XV, part II, E. Wunsch, Ed., George Theime Verlag, 1974, Stuttgart. Separation of unwanted side products and purification of intermediates is achieved by chromatography on silica gel, employing flash chromatography (W. C. Still, M. Kahn and A. Mitra, J. Org. Chem. 43 2923 1978), by crystallization, or by trituration. Transformation of 1-3 into an intermediate of Formula 1-4 can be carried out by removal of the protecting group Prt as described above.

SCHEME 2

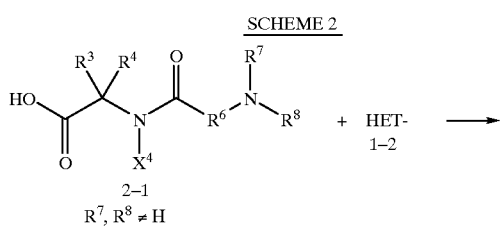

As illustrated in Scheme 2, coupling of a heterocyclic amine of Formula 1-2, as defined in claim 1, with an amino acid of Formula 2-1, where $R^7$ and $R^8$ are not hydrogen, is conveniently carried out in a manner similar to that described in Scheme 1.

SCHEME 3

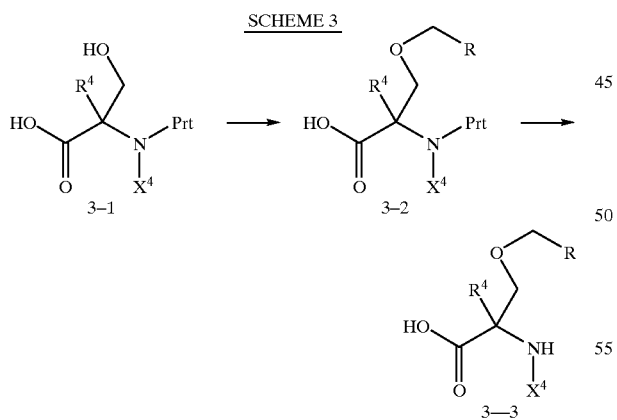

As illustrated in Scheme 3, an intermediate ether of Formula 3-2 can be prepared by treating an amino acid of Formula 3-1, where Prt is a suitable protecting group, with a base such as potassium carbonate or sodium hydride followed by an alkyl halide, benzyl halide, tosylate or mesylate such as benzylbromide in a suitable solvent such as DMF or THF. Deprotection of the amine transforms 3-2 into 3-3. Alternatively, many amino acids of Formula 3-3 are commercially available. R is a group defined for $R^3$ in Formula I, above.

SCHEME 4

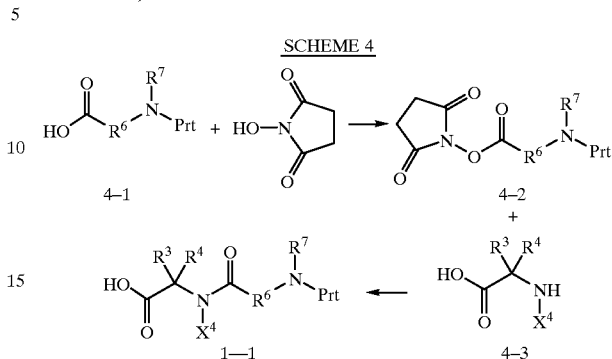

As illustrated in Scheme 4, intermediates of Formula 4-2 can be prepared by treating an acid of Formula 4-1 with hydroxysuccinimide in the presence of a coupling agent such as EDC in an inert solvent such as methylene chloride. Treating 4-2 with an amino acid of Formula 4-3 in a solvent such as DMF in the presence of a base such as diisopropylethylamine produces compounds of Formula 1-1.

SCHEME 5

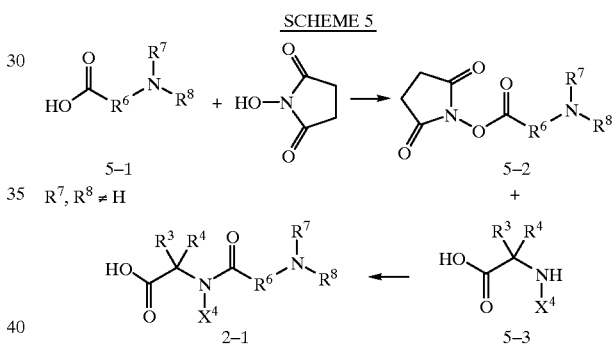

As illustrated in Scheme 5, dipeptides of Formula 2-1, where $R^7$ and $R^8$ are not hydrogen, is conveniently synthesized by the procedures described in Scheme 4.

SCHEME 6

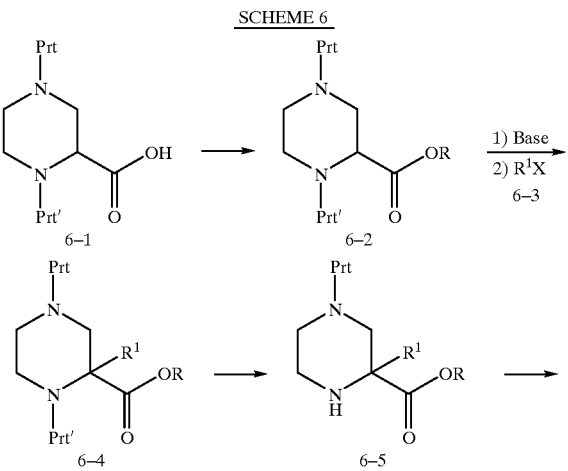

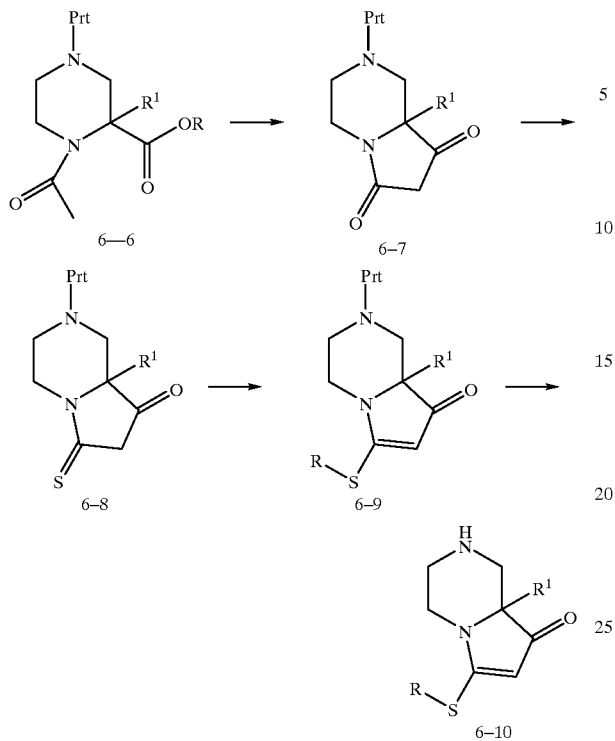

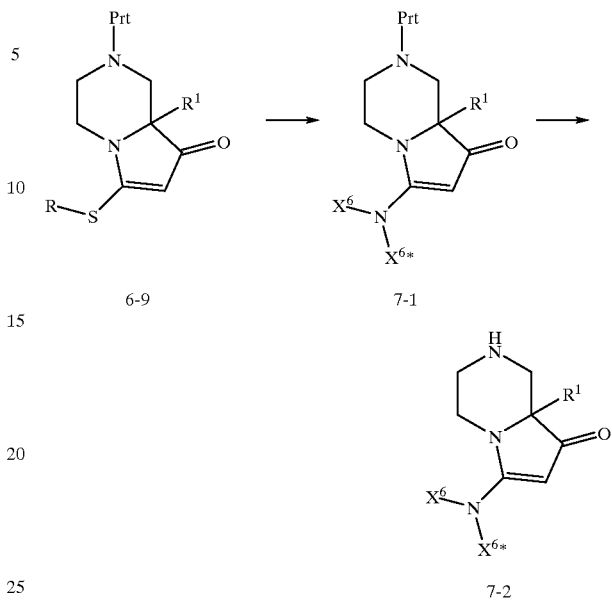

SCHEME 7

Intermediate esters of Formula 6-2, where Prt and Prt' are protecting groups, can be prepared by treating an acid of Formula 6-1 with a base such as potassium carbonate followed by an alkyl halide such as iodomethane in a suitable solvent such as DMF. Alternatively, an ester of Formula 6-2 can be prepared by reacting an acid of Formula 6-1 with diazomethane or (trimethylsilyl)diazomethane. For the preparation of compound 6-2 see Bigge, C. F. et al., Tet. Lett., 1989, 30, 5193–5196. Intermediate 64 is generated by alkylating ester 6-2 with a reagent such as an alkyl halide, tosylate or mesylate with a suitable strong base such as NaHMDS, in a suitable solvent system such as DMF/THF at a temperature of about −78° C.

Transformation of intermediate 6-4 to 6-5 can be achieved by removal of the protecting group Prt' as described above. Amine 6-5 can then be acetylated, such as with acetyl chloride in the presence of a tertiary amine base, preferably diisopropylethylamine, in an appropriate solvent like methylene chloride to give 6-7. Cyclization of a compound of Formula 6-6 occurs upon treating 6-6 with a strong base such as LHMDS at a suitable temperature, about −78° C. to 40° C., to produce an intermediate of Formula 6-7. Treatment of 6-7 with a reagent like $P_2S_5$ or with Lawesson's reagent in a solvent such as toluene at a suitable temperature, about 70° C. to reflux, can provide compounds of Formula 6-8 (see T. Naito et al. Heterocycles 1996, 24, 2117). Alkylation of 6-8 to give 6-9 can be achieved by deprotonating 6-8 with a base like sodium hydride or an alkali metal alkoxide like sodium methoxide followed by treatment with an alkylating agent such as an alkyl halide, mesylate or tosylate, for instance methyl iodide (R. Raap Can. J. Chem. 1968, 46, 2255). The product, 6-9, may then be deprotected, as described above, to provide 6-10. One skilled in the art will recognize that $R^2$ substitution could have been introduced adjacent to the carbonyl of 6-10 by alkylating ketoamide 6-7.

Intermediates of Formula 7-1 may be prepared by heating 6-9, preferably when R is $CH_3$, with a primary or secondary amine at about 70° C. to 120° C. (cf. M. Hojo et al. Synthesis 1990, 195). The product, 7-1, may then be deprotected, as described above, to provide 7-2. One skilled in the art will recognize that $R^2$ substitution could have been introduced adjacent to the carbonyl of 7-2 by alkylating ketoamide 6-7.

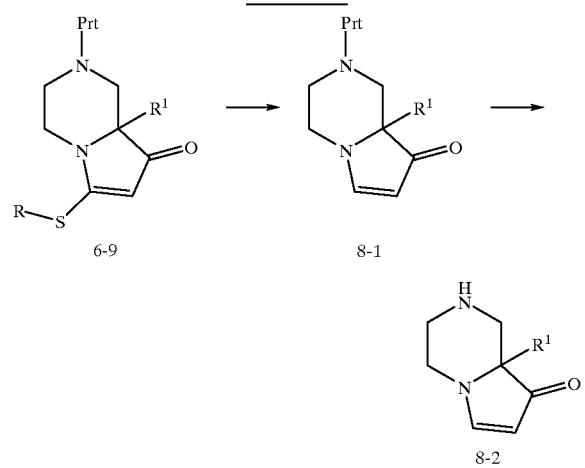

SCHEME 8

Intermediates of Formula 8-1 may be prepared by treating 6-9, preferably when R is $CH_3$, with Raney-nickel in a suitable solvent like methanol (Monotsh. Chem. 1995, 126, 1367). The product, 8-1, may then be deprotected, as described above, to provide 8-2. One skilled in the art will recognize that $R^2$ substitution could have been introduced adjacent to the carbonyl of 8-2 by alkylating ketoamide 8-7.

SCHEME 9

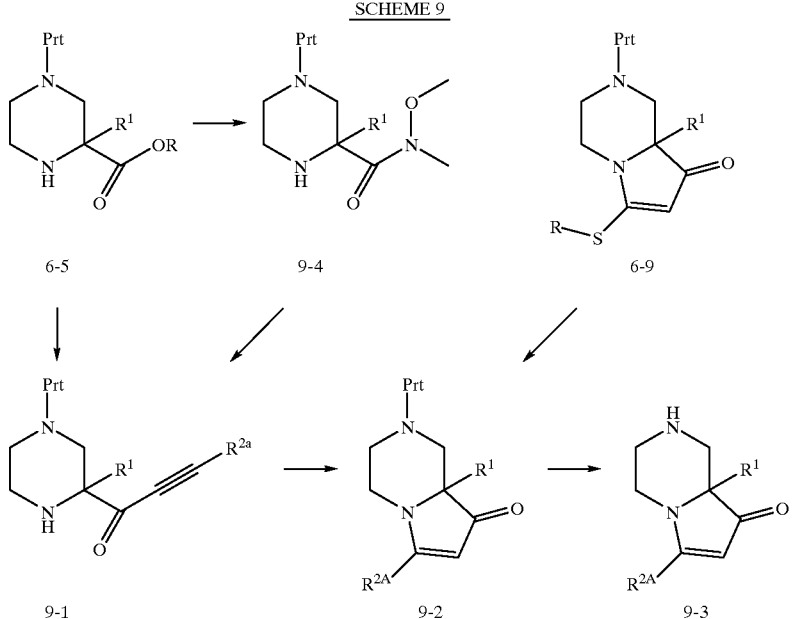

Intermediates of Formula 9-2 can be generated by treating 6-5 with an alkynyl metal reagent, such as propynyl lithium, at a suitable temperature of about −100° C. to −50° C., preferably −78° C., to give, after quenching with a proton source such as methanol, intermediate 9-1 which can then cyclize under the reaction conditions. Amide 94, available from 6-1, 6-2, or 6-3 using standard methodology, could also be treated with an alkynyl metal reagent to produce 9-2 by way of 9-1. Conjugate addition of an alkyl metal reagent, such as a cuprate, or the addition of an enolate, such as the alkali metal derivative of a ketonitrile (P. Patra et al. Tetrahedron Lett. 1977, 38, 3119), to 6-9 can also provide a route to 9-2. The product, 9-2, may then be deprotected, as described above, to provide 9-3.

SCHEME 10

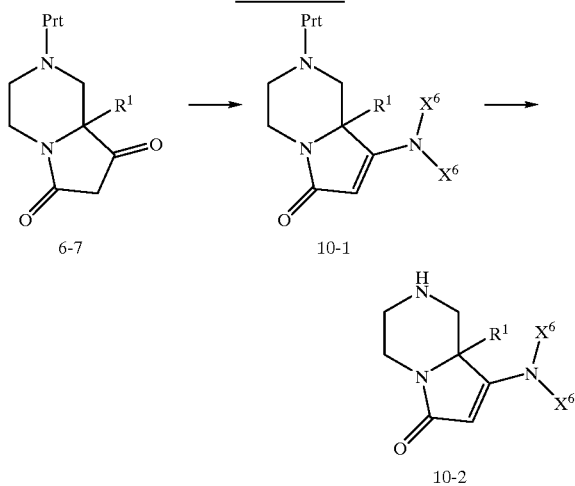

Intermediates of Formula 10-1 may be prepared by heating 6-7 with a primary or secondary amine at about 70° C. to 120° C. (cf. J. W. Patterson et al. J. Med. Chem. 1992, 35, 507; Pharmazie 1977, 32, 572). The product, 10-1, may then be deprotected, as described above, to provide 10-2. One skilled in the art will recognize that $R^2$ substitution could have been introduced adjacent to the carbonyl of 10-2 by alkylating ketoamide 6-7.

SCHEME 11

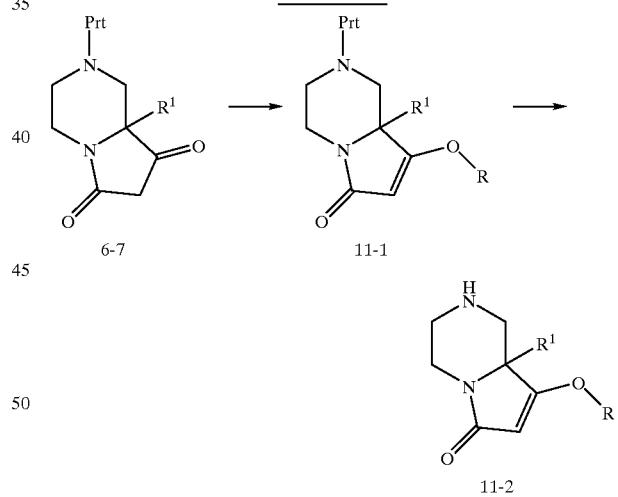

Intermediates of Formula 11-1, where R=CH$_3$, may be prepared by treating 6-7 with diazomethane or (trimethylsilyl)diazomethane. Alternatively, deprotonation of 6-7 followed by treatment with the appropriate alkylating agent can give O-alkylation to produce 11-1 (R=alkyl). Treatment of 6-7 with an alcohol, ROH, in the presence of a suitable acid catalyst may also produce 11-1. The product, 11-1, may then be deprotected, as described above, to provide 11-2. One skilled in the art will recognize that $R^2$ substitution could have been introduced adjacent to the carbonyl of 11-2 by alkylating ketoamide 6-7.

SCHEME 12

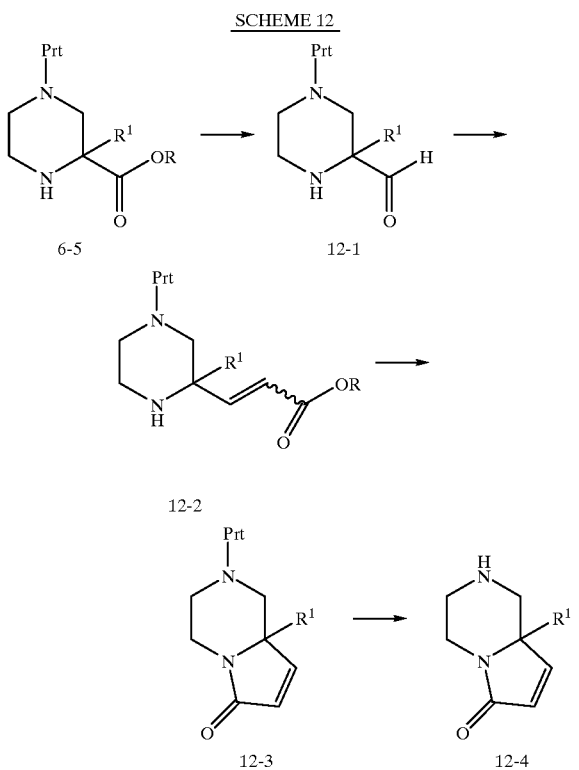

Aldehydes of Formula 12-1 can be prepared by reducing 6-5 with an agent like diisobutylaluminum hydride at a suitable temperature, preferably −78° C. to 0° C. in a suitable solvent, such as THF, methylene chloride, toluene or ether. Aldehyde 12-1 may then be olefinated with a reagent such as the anion generated upon treating a trialkylphosphono acetate with an appropriate base, such as NaHMDS in a suitable solvent, such as THF. The olefin, if of the cis configuration, can directly cyclize to give 12-3. The trans olefin can react by conjugate addition of an amine or alkoxide, cyclization of the β-substituted ester and then elimination of the amine or alkoxide, such as by heating with sodium methoxide in methanol at reflux, to also afford 12-3.

The product, 12-3, may then be deprotected, as described above, to provide 12-4.

SCHEME 13

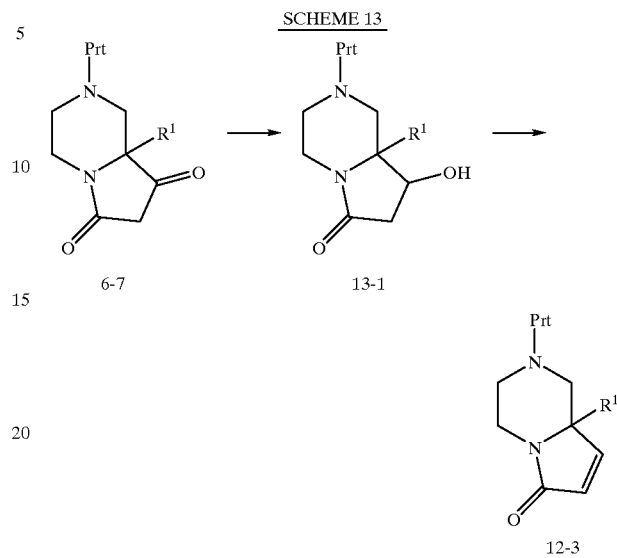

An alternate synthesis of 12-3 is shown above. Reduction of ketoamide 6-7 with a reducing agent such sodium borohydride, in an reaction inert solvent such as methanol at a suitable temperature such as 0° C. affords alcohol 13-1. The alcohol is reacted under standard elimination conditions well known to those skilled in the art to provide unsaturated lactam 12-2. Suitable elimination conditions include activating the alcohol, such as by converting it to the corresponding tosylate or mesylate, and then treating the activated alcohol with base at a suitable temperature, for instance with 1,8-diazabicyclo[5.4.0]undec-7-ene in refluxing toluene, or by deprotonating the amide with a strong base such as LHMDS. The alcohol may also be eliminated at suitable temperatures in the presence of a strong base or strong acid. Those skilled in the art will recognize that these conditions may also cleave the protecting group (P).

SCHEME 14

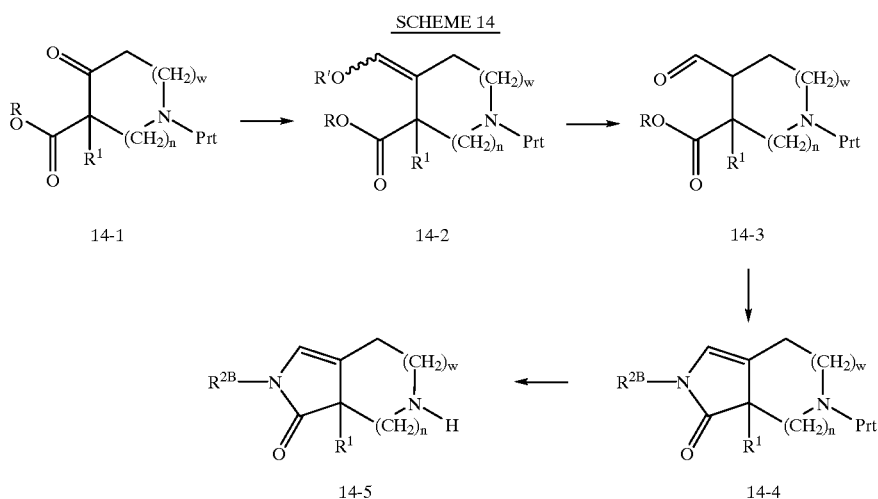

Intermediate enol ethers of Formula 14-2 can be prepared by treating 14-1 (R is an alkyl group, prepared as described in Carpino et. al, (WO 9724369) with a reagent, such as methoxymethyl triphenylphosphonium chloride (R'=Me) and a strong base, such as potassium tert-butoxide, in a suitable solvent such as THF. Hydrolysis of an enol ether of Formula 14-2 under acidic conditions produces an aldehyde of the Formula 14-3. Conversion of the aldehyde to the corresponding imine with a primary amine ($R^{2B}NH_2$) and concomitant loss of water, followed by isomerization to the corresponding enamime, for example with acid and heat, and cyclization affords 14-4. Deprotection of the nitrogen as described above affords 14-5. One skilled in the art will recognize that an $R^{1A}$ substituent could have been introduced by alkylating the ketone 14-1 and/or aldehyde 14-3.

GENERAL EXPERIMENTAL PROCEDURES

Silica gel was used for column chromatography. Melting points were taken on a Buchi 510 apparatus and are uncorrected. Proton and carbon NMR spectra were recorded on a Varian XL-300, UNITYPlus-400, Bruker AC-300, or Bruker AC-250 at 25° C. Chemical shifts are expressed in parts per million downfield from trimethylsilane. Particle beam mass spectra (PBMS) were obtained on a Hewlett-Packard 5989A spectrometer using ammonia as the source of chemical ionization. The protonated parent ion is reported as $(M+H)^+$. For initial sample dissolution chloroform or methanol was employed. Atmospheric Pressure Chemical Ionization mass spectra (APcI MS) were obtained on a Platform II by Fisons (now called Micromass Inc.) instrument. They are either run via +APcI (basic method) or –APcI (acid method). The mobile phase is 50:50 $H_2O$:acetonitrile. Either a protonated parent $(+APcI)$ or deprotonated parent ion $(-APcI)$ is observed (reported as $(M+H)^+$ or $(M-H)^-$). For initial sample dissolution, chloroform or methanol was employed. Thermospray mass spectra (TSMS) were obtained on a Trio-1000 by Fisions spectrometer using 0.1 M ammonium acetate in 1/4 water/methanol. The protonated parent ion is reported as $(M+H)^+$. For initial sample dissolution chloroform or methanol were employed. TLC analyses were performed using E. Merck Kieselgel 60 F254 silica plates visualized (after elution with the indicated solvent(s)) by UV, iodine or by staining with 15% ethanolic phosphomolybdic acid or ceric sulfate/ammonium molybdate and heating on a hot plate. The terms "concentrated" and "coevaporated" refer to removal of solvent at water aspirator pressure on a rotary evaporator with a bath temperature of less than 40° C.

The following examples are provided for the purpose of further illustration only and are not intended to be limitations on the disclosed invention.

General Procedure A (Peptide coupling using PPAA). A 0° C. 0.1–0.5 M solution or suspension of the secondary amine or amine hydrochloride (about 1.0 equivalent) in EtOAc was treated sequentially with triethylamine (about 5 equivalents), and then about 1.0–1.2 equivalents of the carboxylic acid coupling partner. After stirring about 20–30 minutes, a 50% solution of PPAA in EtOAc (about 1.2–1.5 equivalents) was added dropwise and the mixture was stirred for about 2–18 hours in an ice bath (the ice bath was allowed to melt, thus the reaction mixture was typically held at about 0–20° C. for about 4–6 hours and about 20–25° C. for the remaining period). The mixture was diluted with ethyl acetate or other solvent as specified, and the resulting mixture washed times with saturated sodium bicarbonate (the aqueous phase being sometimes back-washed with ethyl acetate), once with brine, dried over $Na_2SO_4$ or $MgSO_4$, and concentrated giving the crude product which was purified as specified.

General Procedure B. (Cleavage of a t-BOC-protected amine using concentrated HCl). The t-Boc amine was dissolved in a minimum volume of ethanol and the resulting solution was cooled to about 0° C. and concentrated HCl (typically about 1–4 mL per mmol amine) was added and the reaction was warmed to room temperature and stirred for about 1–2.5 hours (the time required for complete disappearance of the starting material to a more polar product as judged by TLC). The resulting solution or suspension was concentrated, and the residue coevaporated several times with added ethanol to give the free amine which was used without further purification or purified as specified.

General Procedure C. (Cleavage of a t-BOC-protected amine using TFA). Trifluoroacetic acid (usually at about 0–25° C.) was added to the t-Boc amine (typically about 10 mL per mmol amine) neat or dissolved in a minimum volume of dichloromethane and the resulting solution was stirred at about 0° C. or at room temperature for 0.25–2 hours (the time required for complete disappearance of the starting material to a more polar product as judged by TLC). The resulting solution or suspension was concentrated, and the residue coevaporated several times with added methylene chloride. The residue was then dissolved in ethyl acetate and washed twice with 1N NaOH and once with brine. The organic phase was then dried over $Na_2SO_4$ and evaporated to give the free amine which was used without further purification or purified as specified.

General Procedure D. (Cleavage of a benzyl-protected amine using 10% palladium on carbon). The benzyl amine, ethanol (typically about 1 mL per every 0.03–0.08 mmol of amine), and 10% palladium on carbon (typically about 20–100% of the weight of the amine used) were combined and hydrogenated at about 40–50 psi hydrogen on a Parr® shaker overnight. The mixture was then filtered through a bed of Celite®. The Celite® was washed with ethanol, and the filtrate was concentrated in vacuo to give the de-benzylated amine which was used without further purification or purified as specified.

General Procedure E. (Cleavage of a CBZ-protected amine using 10% palladium on carbon) The CBZ amine, ethanol (typically about 1 mL per every 0.03–0.08 mmol of amine), and 10% palladium on carbon (typically about 20–100% of the weight of the amine used) were combined and hydrogenated at about 40–50 psi hydrogen on a Parr® shaker overnight. The mixture was then filtered through a bed of Celite®. The Celite® was washed with ethanol, and the filtrate was concentrated in vacuo to give the de-benzylated amine which was used without further purification or purified as specified.

EXAMPLE 1

2-Amino-N-{1(R)-benzyloxymethyl-2-[8a(S)-(4-fluoro-benzyl)-6-methylsulfanyl-8-oxo-3,4,8,8a-tetrahydro-1H-pyrrolo[1,2-a]pyrazin-2-yl]-2-oxo-ethyl}-2-methyl-propionamide, hydrochloride

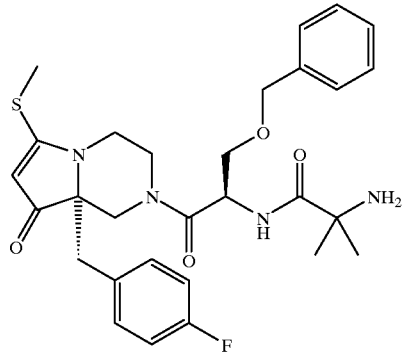

A. 2-(4-Fluoro-benzyl)-piperazine-1,2,4-tricarboxylic acid 1-benzyl ester 4-tert-butyl ester 2-methyl ester To a stirred solution of piperazine-1,2,4-tricarboxylic acid 1-benzyl ester 4-tert-butyl ester 2-methyl ester (10.5 g, 27.8 mmol), prepared as described by Bigge et al. (Tetrahedron Let. 1989, 30, 5193), in tetrahydrofuran (200 mL) under a nitrogen atmosphere was added N,N-dimethylformamide (30 mL). The reaction was cooled to about −78° C., and a 0.5 M solution of potassium bis(trimethylsilyl)amide in toluene (83 mL, 42 mmol) was added. The reaction was stirred at about −78° C. for about 1 hour, and then 4-fluorobenzyl bromide (5.2 mL, 42 mmol) was added. The reaction was stirred for about 1 hour more at about −78° C., then warmed to room temperature and stirred overnight. The reaction was quenched with saturated sodium bicarbonate solution, and the mixture was extracted three times with ethyl acetate. The combined organic layers were extracted twice with water, brine, dried over anhydrous magnesium sulfate, filtered and concentrated in vacuo to give the crude product as a yellow oil. Purification by silica gel chromatography using 0–20% ethyl acetate/hexanes as eluent afforded the title compound of part 1-A (8.54 g, 63%) as a colorless oil: +APcI MS (M−Boc+H)$^+$ 387; $^1$H NMR=400 MHz (CDCL$_3$) δ: 7.45–7.30 (arom, br s, 5H), 7.00–6.80 (arom, br m, 4H), 5.35–5.05 (br m, 2H), 2.53 (br t, 1H), 1.40 (Boc, s, 9H).

B. 3-(4-Fluoro-benzyl)-piperazine-1,3-dicarboxylic acid 1-tert-butyl ester 3-methyl ester According to General Procedure E, the title compound of part 1-A (0.249 g, 0.72 mmol) was deprotected to give the title compound of part 1-B (0.230 9, 91%): +APcI MS (M+H)$^+$ 353, (M−$^t$Bu+H)$^+$ 297, (M−Boc+H)$^+$ 253; $^1$H NMR=400 MHz (CDCl$_3$) δ: 7.08–6.90 (arom, m, 4H), 3.62 (Me, s, 3H), 1.41 (Boc, s, 9H).

C. 4-Acetyl-3-(4-fluoro-benzyl)-piperazine-1,3-dicarboxylic acid 1-tert-butyl ester 3-methyl ester To a stirred solution of the title compound of part 1-B (5.0 g, 14 mmol) and diisopropylethylamine (9.9 mL, 57 mmol) in dichloromethane (100 mL) under a nitrogen atmosphere was added acetyl chloride (2.0 mL, 28 mmol). The reaction was stirred for about 15 hours, then quenched with saturated aqueous NaHCO$_3$. Additional methylene chloride was added and the mixture was washed twice with saturated NaHCO$_3$, then brine, dried over anhydrous magnesium sulfate, filtered and concentrated in vacuo to give the crude title compound of part 1-C (5.6 g, quantitative): +APcI MS (M−$^t$Bu+H)$^+$ 339, (M−Boc+H)$^+$ 295; $^1$H NMR=400 MHz (CDCl$_3$) δ: 7.10–7.69 (arom., m, 4H), 3.70 (MeO, d, 3H), 2.10 (MeCO, d, 3H), 1.42 (BOC, d, 9H).

D. 8a-(4-Fluoro-benzyl)-6,8-dioxo-hexahydro-pyrrolo[1,2-a]pyrazine-2-carboxylic acid tert-butyl ester To a stirred solution of the title compound of part 1-C (5.6 g, 0.22 mmol) in anhydrous tetrahydrofuran (50 mL) cooled to about −78° C. under nitrogen atmosphere was added a 1M solution of lithium bis(trimethylsilyl)amide in tetrahydrofuran (42.6 mL, 42.6 mmol) dropwise. The reaction was stirred at −78° C. for 1 hour, then the reaction was quenched with methanol and concentrated in vacuo. Ethyl acetate was added, and the mixture was extracted with saturated sodium bicarbonate solution, brine, dried over anhydrous magnesium sulfate, filtered and concentrated in vacuo to give crude product. Purification by silica gel chromatography using 50% ethyl acetate/hexanes as eluent yielded the title compound of part 1-D (3.4 g, 66%): −APcI MS (M−H)$^-$ 361; $^1$H NMR=400 MHz (CDCl$_3$) δ: 6.94 (arom., d, 4H), 4.35 (dd, 1H), 2.66 (CH$\underline{H}$Ph, d, 1H), 2.01 (CH$\underline{H}$Ph, d, 1H), 1.47 (BOC, s, 9H).

E. 8a-(4-Fluoro-benzyl)-8-oxo-6-thioxo-hexahydro-pyrrolo[1,2-a]pyrazine-2-carboxylic acid tert-butyl ester To a stirred solution of the title compound of part 1-D (1.0 g, 2.8 mmol) in toluene (20 mL) under a nitrogen atmosphere was added Lawesson's reagent (0.57 g, 1.4 mmol). The reaction was heated 1 hour at 100° C., cooled, diluted with ethyl acetate and washed with brine (3×), dried over anhydrous magnesium sulfate, and then concentrated in vacuo. Purification by silica gel chromatography using 0–30% ethyl acetate/hexanes as eluent yielded the title compound of part 1-E (0.55 g, 52%) as a colorless solid: −APcI MS (M−H)$^-$ 377; $^1$H NMR=400 MHz (CDCl$_3$) δ: 6.99–6.90 (arom, m, 4H), 5.21 (dd, 1h), 3.24 (CH$\underline{H}$Ph, d, 1H), 2.50 (CH$\underline{H}$Ph, d, 1H), 1.50 (BOC, s, 9H).

F. 8a-(4-Fluoro-benzyl)-6-methylsulfanyl-8-oxo-3,4,8,8a-tetrahydro-1H-pyrrolo[1,2-a]pyrazine-2-carboxylic acid tert-butyl ester To a stirred solution of the title compound of part 1-E (0.55 g, 1.4 mmol) in methanol (5 mL) under a nitrogen atmosphere was added, dropwise, a solution of sodium methoxide (93 mg, 1.7 mmol) in methanol (10 mL), followed by the dropwise addition of methyl iodide (0.13 mL, 2.0 mmol). After stirring about 16 hours the reaction was concentrated in vacuo, redissolved in methylene chloride, washed with saturated aqueous sodium bicarbonate, dried over anhydrous magnesium sulfate, and then concentrated in vacuo to give the title compound of part 1-F (0.56 g, 98%) as a colorless solid: +APcI MS (M+H)$^+$ 393; $^1$H NMR=400 MHz (CDCl$_3$) δ: 7.08–7.00 (arom, m, 2H), 6.89–6.81 (arom, m, 2H), 5.02 (s, 1H), 3.73 (dd, 1H), 3.19 (CH$\underline{H}$Ph, d, 1H), 3.03 (CH$\underline{H}$Ph, d, 1H), 2.37 (CH$_3$S, s, 3H), 1.49 (BOC, s, 9H).

G. 8a-(4-Fluoro-benzyl)-6-methylsulfanyl-1,3,4,8a-tetrahydro-2H-pyrrolo[1,2-a]pyrazin-8-one, hydrochloride The title compound of part 1-F (50 mg, 0.13 mmol) was deprotected according to the method described in General Procedure B to give the title compound of part 1-G (37 mg, quantitative): +APcI MS (M+H)$^+$ 293; $^1$H NMR=400 MHz (methanol-d$_4$) δ: 7.15–6.88 (arom., series of m, 4H), 4.14 (br d, 1H), 3.46 (d, 1H), 2.44 (CH$_3$S, s, 3H).

H. (1-{1(R)-Benzyloxymethyl-2-[8a(S)-(4-fluoro-benzyl)-6-methylsulfanyl-8-oxo-3,4,8,8a-tetrahydro-1H-pyrrolo[1,2-a]pyrazin-2-yl]-2-oxo-ethylcarbamoyl}-1-methyl-ethyl)-carbamic acid tert-butyl ester According to General Procedure A, the title compound of part 1-G (37 mg, 0.13 mmol) was coupled to 3(R)-benzyloxy-2-(2-tert-butoxycarbonylamino-2-methyl-propionyl-amino)-propionic acid (58 mg, 0.15 mmol), prepared according to the method of Carpino et al. (WO 97/24369), and the product was purified by silica gel chromatography using 1:1:0 to 1:0:0 to 97:0:3 ethyl acetate/hexanes/methanol as eluent to give a 2:1 mixture of the desired isomer of the title compound of part 1-H and the less polar diastereomer (5 mg, 6%), fractions which contained a nearly 1:1 mixture of the two diastereomers, followed by the 3:1 mixture of the more polar diastereomer and 1-H (14 mg, 17%). 1-H: +APcI MS (M+H)+ 655; $^1$H NMR=400 MHz (CDCl$_3$) δ: 7.35–6.65 (arom., series of m, 9H), 4.47 (PhC$\underline{H}_2$O, ABq, 2H), 2.61 (d, 1H), 2.39 (C$\underline{H}_3$S, s, 3H). For isomer: $^1$H NMR=400 MHz (CDCl$_3$) δ: 7.35–6.65 (arom., series of m, 9H), 4.58 (PhCH$\underline{H}$O, d, 1H), 4.48 (PhCH$\underline{H}$O, d, 1H), 2.53 (d, 1H), 2.34 (C$\underline{H}_3$S, s, 3H).

I. 2-Amino-N-{1(R)-benzyloxymethyl-2-[8a(S)-(4-fluoro-benzyl)-6-methylsulfanyl-8-oxo-3,4,8,8a-tetrahydro-1H-pyrrolo[1,2-a]pyrazin-2-yl]-2-oxo-ethyl}-2-methyl-propionamide, hydrochloride The title compound of part 1-H (5 mg, 0.008 mmol) was deprotected according to the method described in General Procedure B, and the product was triturated with ethyl ether to give a 2:1 mixture of the title compound of Example 1 and the 8a(R) diastereomer (4 mg, 80%). Title compound of Example 1: +APcI MS (M+H)$^+$ 555; $^1$H NMR=400 MHz (methanol-d$_4$) δ: 7.40–6.87 (arom., series of m, 9H), 5.13 (t, 1H), 4.53 (s, 2H), 2.44 (s, 3H), 1.63–1.50 (Me, m, 6H).

EXAMPLE 2

2-Amino-N-{1(R)-benzyloxymethyl-2-[8a(S)-(4-fluoro-benzyl)-8-oxo-6-pyrrolidin-1-yl-3,4,8,8a-tetrahydro-1H-pyrrolo[1,2-a]pyrazin-2-yl]-2-oxo-ethyl}-2-methyl-propionamide, hydrochloride

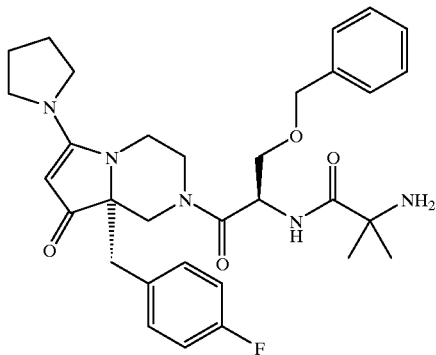

A. 8a-(4-Fluoro-benzyl)-8-oxo-6-pyrrolidin-1-yl-3,4,8,8a-tetrahydro-1H-pyrrolo[1,2-a]pyrazine-2-carboxylic acid tert-butyl ester A stirred solution of the title compound of part 1-F (0.15 g, 0.38 mmol) in pyrollidine (0.63 mL) under nitrogen was heated to 100° C. After stirring about 16 hours the reaction was cooled, concentrated in vacuo, redissolved in ethyl acetate, washed with saturated aqueous sodium bicarbonate and then brine, dried over anhydrous magnesium sulfate, and then concentrated in vacuo to give the title compound of part 2-A (0.14 g, 90%): +APcI MS (M+H)$^+$ 416; $^1$H NMR= 400 MHz (CDCl$_3$) δ: 7.09 (arom, m, 2H), 6.83 (arom, m, 2H), 4.43 (m, 1H), 2.98 (br t, 1H), 1.93 (br s, 1H), 1.63 (br s, 1H), 1.46 (BOC, s, 9H).

B. 8a-(4-Fluoro-benzyl)-6-pyrrolidin-1-yl-1,3,4,8a-tetrahydro-2H-pyrrolo[1,2-a]pyrazin-8-one, hydrochloride The title compound of part 2-A (140 mg, 0.34 mmol) was deprotected according to the method described in General Procedure B to give the title compound of part 2-B (141 mg, quantitative): +APcI MS (M+H)$^+$ 316; $^1$H NMR=400 MHz (methanol-d$_4$) δ: 7.21 (arom., dd, 2H), 7.01(arom., t, 2H), 4.66 (dd, 1H), 3.87 (d, 1H), 3.38 (d, 1H), 3.16 (d, 1H).

C. (1-{1(R)-Benzyloxymethyl-2-[8a(S)-(4-fluoro-benzyl)-8-oxo-6-pyrrolidin-1-yl-3,4,8,8a-tetrahydro-1H-pyrrolo[1,2-a]pyrazin-2-yl]-2-oxo-ethylcarbamoyl}-1-methyl-ethyl)-carbamic acid tert-butyl ester According to General Procedure A, the title compound of part 2-B (35 mg, 0.11 mmol) was coupled to 3(R)-benzyloxy-2-(2-tert-butoxycarbonylamino-2-methyl-propionyl-amino)-propionic acid (50 mg, 0.13 mmol) and the product was purified by silica gel chromatography using 0-5-10% methanol/ethyl acetate as eluent to give the desired isomer of the title compound of part 2-C (8 mg, 11%), followed by the more polar diastereomer (10 mg, 14%). 2-C: +APcI MS (M+H)$^+$ 678; $^1$H NMR=400 MHz (CDCl$_3$) δ: 7.40–6.70 (arom., series of m, 9H), 4.47 (PhC$\underline{H}_2$O, ABq, 2H), 1.96 (br s, 2H), 1.41 (CH$_3$, m, 6H), 1.32 (BOC, s, 9H). For isomer: $^1$H NMR=400 MHz (CDCl$_3$) δ: 7.38–6.70 (arom., series of m, 9H), 4.61 (PhCH$\underline{H}$O, d, 1H), 4.50 (PhCH$\underline{H}$O, d, 1H), 1.94 (br s, 2H), 1.44 (CH$_3$, m, 6H), 1.39 (BOC, s, 9H).

D. 2-Amino-N-{1(R)-benzyloxymethyl-2-[8a(S)-(4-fluoro-benzyl)-8-oxo-6-pyrrolidin-1-yl-3,4,8,8a-tetrahydro-1H-pyrrolo[1,2-a]pyrazin-2-yl]-2-oxo-ethyl}-2-methyl-propionamide, hydrochloride The title compound of part 2-C (5 mg, 0.008 mmol) was deprotected according to the method described in General Procedure B, and the product was triturated with ethyl ether to give the title compound of Example 2 (4.6 mg, 98%) as a solid: +APcI MS (M+H)$^+$ 578; $^1$H NMR=400 MHz (methanol-d$_4$) δ: 7.40–6.93 (arom., series of m, 9H), 5.15 (m, 1H), 4.55 (s, 2H), 4.38 (d, 1H), 2.99 (d, 1H), 1.59 (CH$_3$, m, 6H).

EXAMPLE 3

2-Amino-N-{1(R)-benzyloxymethyl-2-[8a(S)-(4-fluoro-benzyl)-8-oxo-3,4,8,8a-tetrahydro-1H-pyrrolo[1,2-a]pyrazin-2-yl]-2-oxo-ethyl}-2-methyl-propionamide, hydrochloride

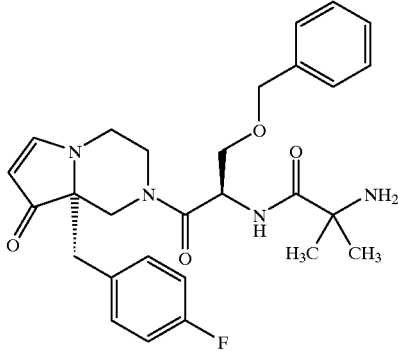

A. 8a-(4-Fluoro-benzyl)-8-oxo-3,4,8,8a-tetrahydro-1H-pyrrolo[1,2-a]pyrazine-2-carboxylic acid tert-butyl ester To a stirred solution of the title compound of part 1-F (450 mg, 1.15 mmol) in ethanol (10 mL) was added Raney Nickel (1.5 g, 50% slurry in water) in several portions. After stirring about 2.5 days the reaction was filtered, concentrated in vacuo, redissolved in ethyl acetate, washed with brine, dried over anhydrous magnesium sulfate, and then concentrated in vacuo to give the title compound of part 3-A (0.35 g, 88%): +APcI MS (M+H)$^+$ 347; $^1$H NMR=400 MHz (CDCl$_3$) δ: 7.60 (COCH=C$\underline{H}$, d, 1H), 7.03 (arom, dd, 2H), 6.83 (arom, t, 2H), 4.99 (COC$\underline{H}$=CH, d, 1H), 3.22 (d, 1H), 3.00 (d, 1H), 1.49 (BOC, s, 9H).

B. 8a-(4-Fluoro-benzyl)-1,3,4,8a-tetrahydro-2H-pyrrolo[1,2-a]pyrazin-8-one, hydrochloride The title compound of part 3-A (0.32 g, 0.92 mmol) was deprotected according to the method described in General Procedure B to give the title compound of part 3-B (0.30 g, quantitative): +APcI MS (M+H)+ 247; ¹H NMR=400 MHz (methanol-d₄) δ: 8.11 (COCH=C<u>H</u>, br s, 1H), 7.14 (arom, m, 2H), 6.92 (arom, m, 2H), 4.12 (dd, 1H), 3.05 (d, 1H).

C. (1-{1(R)-Benzyloxymethyl-2-[8a(S)-(4-fluoro-benzyl)-8-oxo-3,4,8,8a-tetrahydro-1H-pyrrolo[1,2-a]pyrazin-2-yl]-2-oxo-ethylcarbamoyl}-1-methyl-ethyl)-carbamic acid tert-butyl ester According to General Procedure A, the title compound of part 2-B (25 mg, 0.10 mmol) was coupled to 3(R)-benzyloxy-2-(2-tert-butoxycarbonylamino-2-methyl-propionyl-amino)-propionic acid (48 mg, 0.15 mmol) and the product was purified by silica gel chromatography using 50-25-0% hexanes/ethyl acetate as eluent to give the desired isomer of the title compound of part 2-C (3.5 mg, 6%), followed by the more polar diastereomer (7 mg, 12%). 3-C: +APcI MS (M+H)+ 609; ¹H NMR=400 MHz (CDCl₃) δ: 7.57 (COCH=C<u>H</u>, d, 1H), 7.43–6.75 (arom., series of m, 9H), 5.01 (COC<u>H</u>=CH, br s, 1H), 4.46 (PhC<u>H</u>₂O, ABq, 2H), 3.17 (d, 1H), 2.50 (d, 1H), 1.46 (CH₃, s, 6H), 1.35 (BOC, s, 9H). For isomer: ¹H NMR=400 MHz (CDCl₃) δ: 7.52 (COCH=C<u>H</u>, d, 1H), 7.35–6.68 (arom., series of m, 9H), 4.94 (COC<u>H</u>=CH, d, 1H), 4.60 (PhCH<u>H</u>O, d, 1H), 4.51 (PhCH<u>H</u>O, d, 1H), 3.13 (d, 1H), 2.41 (d, 1H), 1.44 (CH₃, s, 3H), 1.43 (CH₃, s, 3H), 1.39 (BOC, s, 9H).

D. 2-Amino-N-{1(R)-benzyloxymethyl-2-[8a(S)-(4-fluoro-benzyl)-8-oxo-3,4,8,8a-tetrahydro-1H-pyrrolo[1,2-a]pyrazin-2-yl]-2-oxo-ethyl}-2-methyl-propionamide, hydrochloride The title compound of part 3-C (8.5 mg, 0.014 mmol) was deprotected according to the method described in General Procedure B, and the product was triturated with ethyl ether to give the title compound of Example 3 (6.0 mg, 84%) as a solid: +APcI MS (M+H)+ 509; ¹H NMR=400 MHz (methanol-d₄) δ: 8.49 (N<u>H</u>, d, 1H), 8.27 (COCH=C<u>H</u>, S, 1H), 7.38–6.82 (arom., series of m, 9H), 5.13 (m, 1H), 4.55 (PhC<u>H</u>₂O, s, 2H), 4.43 (br d, 1H), 2.66 (d, 1H), 1.61 (CH₃, s, 3H), 1.60 (CH₃, s, 3H).

EXAMPLE 4

2-Amino-N-[2-(8a(S)-benzyl-6-methyl-8-oxo-3,4,8,8a-tetrahydro-1H-pyrrolo[1,2-a]pyrazin-2-yl)-1(R)-benzyloxymethyl-2-oxo-ethyl]-2-methyl-propionamide, hydrochloride

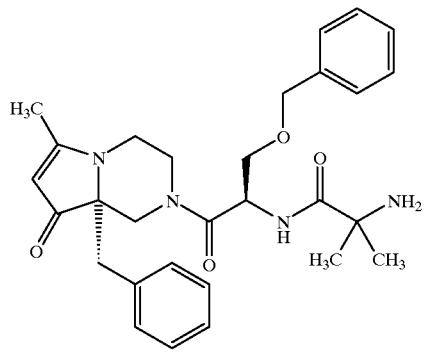

A. 2-Benzyl-piperazine-1,2,4-tricarboxylic acid 1-benzyl ester 4-tert-butyl ester 2-methyl ester To a stirred solution of piperazine-1,2,4-tricarboxylic acid 1-benzyl ester 4-tert-butyl ester 2-methyl ester (20.0 g, 53 mmol) in tetrahydrofuran (500 mL) under nitrogen was added N,N-dimethylformamide (50 mL). The reaction was cooled to about −78° C., and a 1 M solution of sodium bis(trimethylsilyl)amide in tetrahydrofuran (80 mL) was added. The reaction was stirred at about −78° C. for about 1 hour, and then benzyl bromide (9.4 mL, 79 mmol) was added. The reaction was stirred for about 30 minutes more at about −78° C., then warmed to room temperature and stirred overnight. The reaction was quenched with saturated sodium bicarbonate solution, and the mixture was extracted three times with ethyl acetate. The combined organic layers were extracted twice with water, brine, dried over anhydrous magnesium sulfate, filtered and concentrated in vacuo to give 31 g of crude product. Purification by silica gel chromatography using 10–20% ethyl acetate/hexanes as eluent afforded the title compound of part 4-A (20.3 g, 82%): +APcI MS (M−ᵗBu+H)+ 413, (M−Boc+H)+ 369; ¹H NMR=400 MHz (CDCl₃) δ: 7.37 (arom, m, 5H), 7.22 (arom, m, 3H), 7.00 (arom, m, 2H), 1.41 (BOC, d, 9H).

B. 3-Benzyl-piperazine-1,3-dicarboxylic acid 1-tert-butyl ester 3-methyl ester

According to General Procedure E, the title compound of part 4-A (2.8 g, 6.0 mmol) was deprotected to give the title compound of part 4-B (1.89 g, 95%) as a colorless foam: +APcI MS (M+H)+ 335; ¹H NMR=400 MHz (CDCl₃) δ: 7.28–7.18 (arom, m, 5H), 3.66 (Me, s, 3H), 1.40 (Boc, s, 9H).

C. 8a-Benzyl-6-methyl-8-oxo-3,4,8,8a-tetrahydro-1H-pyrrolo[1,2-a]pyrazine-2-carboxylic acid tert-butyl ester To a stirred −78° C. solution of the title compound of part 4-B (1.98 g, 5.93 mmol) in THF (8 mL) under a nitrogen atmosphere was added a 0.25 M solution of propynyl lithium in 1:1 THF/HMPA (23.7 mL), dropwise. After stirring about 1.5 hours the reaction was quenched with saturated aqueous ammonium chloride and the THF was removed in vacuo. The remaining aqueous mixture was then extracted with ethyl acetate, dried over anhydrous magnesium sulfate, and concentrated in vacuo. Purification by silica gel chromatography using 30–70% ethyl acetate/hexanes as eluent afforded the title compound of part 4-C (1.0 g, 50%): +APcI MS (M+H)+ 343; ¹H NMR=400 MHz (CDCl₃) δ: 7.18–7.02 (arom., series of m, 5H), 4.87 (COC<u>H</u>=C, d, 1H), 3.22 (d, 1H), 3.01 (d, 1H), 1.92 (Me, s, 3H), 1.48 (BOC, s, 9H).

D. 8a-Benzyl-6-methyl-1,3,4,8a-tetrahydro-2H-pyrrolo[1,2-a]pyrazin-8-one, hydrochloride The title compound of part 4-C (0.30 g, 0.88 mmol) was deprotected according to the method described in General Procedure B to give the title compound of part 4-D (0.21 g, 86%): +APcI MS (M+H)+ 243; ¹H NMR=400 MHz (methanol-d₄) δ: 7.23–7.08 (arom., series of m, 5H), 3.25–3.10 (m, 3H), 2.19 (Me, s, 3H).

E. {1-[2-(8a(S)-Benzyl-6-methyl-8-oxo-3,4,8,8a-tetrahydro-1H-pyrrolo[1,2-a]pyrazin-2-yl)-1(R)-benzyloxymethyl-2-oxo-ethylcarbamoyl]-1-methyl-ethyl}-carbamic acid tert-butyl ester According to General Procedure A, the title compound of part 4-D (210 mg, 0.88 mmol) was coupled to 3(R)-benzyloxy-2-(2-tert-butoxycarbonylamino-2-methyl-propionyl-amino)-propionic acid (502 mg, 1.32 mmol) and the product was purified by silica gel chromatography using 7:3:0 to 0:1:0 to 0:95:5 hexanes/ethyl acetate/methanol as eluent to give the desired isomer of the title compound of part 4-E (53 mg, 9%), then fractions which contained mixture of the two diastereomers, followed by the more polar diastereomer (102 mg, 17%). 4-E: +APcI MS (M+H)+ 605; ¹H NMR=400 MHz (CDCl₃) δ: 7.35–7.00 (arom., series of m, 10H), 5.18 (m, 1H), 4.96 (s, 1H), 4.86 (s, 1H), 4.44 (PhC<u>H</u>₂O, ABq, 2H), 3.14 (d, 1H), 2.52 (d, 1H), 1.88 (Me, s, 3H), 1.44 (Me, s, 3H), 1.43 (Me, s, 3H), 1.33 (BOC, s, 9H). For isomer: ¹H NMR=400 MHz (CDCl₃) δ: 7.35–6.77 (arom., series of m, 10H), 5.21 (br m, 1H), 3.13 (m, 1H), 2.45 (m, 1H), 1.41 (CH₃, m, 6H), 1.36 (BOC, m, 9H).

F. 2-Amino-N-[2-(8a(S)-benzyl-6-methyl-8-oxo-3,4,8,8a-tetrahydro-1H-pyrrolo[1,2-a]pyrazin-2-yl)-1(R)-benzyloxymethyl-2-oxo-ethyl]-2-methyl-propionamide, hydrochloride The title compound of part 4-E (27 mg, 0.044 mmol) was deprotected according to the method described in General Procedure B, and the product was triturated with ethyl ether to give the title compound of Example 4 (25 mg, quantitative) as a colorless solid: +APcI MS (M+H)+ 505; $^1$H NMR=400 MHz (methanol-$d_4$) δ: 8.52 (NH, d, 1H), 7.40–7.08 (arom., series of m, 10H), 5.17 (m, 1H), 4.55 (PhCH$_2$O, s, 2H), 3.09 (d, 1H), 2.75 (d, 1H), 2.19 (Me, s, 3H), 1.60 (CH$_3$, s, 3H), 1.59 (CH$_3$, s, 3H).

EXAMPLE 5

2-Amino-N-[1(R)-benzyloxymethyl-2-(8-methoxy-6-oxo-8a(R,S)-pyridin-2-ylmethyl-3,4,6,8a-tetrahydro-1H-pyrrolo[1,2-a]pyrazin-2-yl)-2-oxo-ethyl]-2-methyl-propionamide, hydrochloride

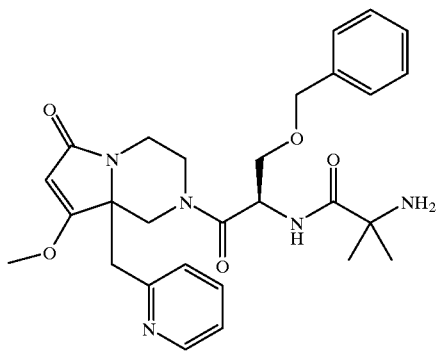

A. 2-Pyridin-2-ylmethyl-piperazine-1,2,4-tricarboxylic acid 1-benzyl ester 4-tert-butyl ester 2-methyl ester A stirred solution of piperazine-1,2,4-tricarboxylic acid 1-benzyl ester 4-tert-butyl ester 2-methyl ester (200 g, 529 mol) in tetrahydrofuran (200 mL) and DMF (1.5 L) was cooled to −78° C. under a nitrogen atmosphere, and a 0.5 M solution of potassium bis(trimethylsilyl)amide in THF (1.27 L) was added. After the above solution had stirred about one hour, the free base of 2-picolyl chloride was generated by extracting the corresponding hydrochloride salt (217 g, 1.32 mol) from saturated sodium bicarbonate solution with methylene chloride. The combined organic extracts were dried (MgSO$_4$), concentrated, immediately dissolved in DMF (100 mL), and then added dropwise to the enolate containing solution. The reaction was stirred for about 4 hours at −78° C., then slowly warmed to room temperature and stirred overnight. The toluene and THF were removed under reduced pressure. The residue was extracted from water (1.5 L) with ethyl acetate (3×1 L), the combined extracts were then washed with water (1.5 L), dried (MgSO$_4$) and then concentrated in vacuo to give 240 g of crude title compound of part 5-A which carried on to the next step: +APcI MS (M+H)+ 470; $^1$H NMR=400 MHz (methanol-$d_4$) δ8.4 (arom, m, 1H), 7.65–7.2 (arom, m, 7H), 6.94 (arom, m, 1H), 5.18 (CbzNCHH, m, 1H), 5.05 (CbzNCHH, m, 1H), 2.54 (m, 1H), 1.41 (Boc, s, 9H).

B. 3-Pyridin-2-ylmethyl-piperazine-1,3-dicarboxylic acid 1-tert-butyl ester 3-methyl ester The crude title compound of part 5-A (240 g) in methanol (1 L), and 10% palladium on carbon (10 g, added in 100 mL water) were combined and hydrogenated at 40–50 psi hydrogen on a Parr® shaker for about 2 days. The mixture was then filtered through a bed of diatomaceous earth. The diatomaceous earth was washed with ethanol, and the filtrate was concentrated in vacuo to give the de-benzylated amine. Two of the above alkylation/reductions were combined and purified by silica gel chromatography using 1:1 ethyl acetate/hexanes to ethyl acetate to 1:9 methanol/ethyl acetate as eluent afforded the title compound of part 5-B (217 g, 61%): +APcI (M+H)+ 336; $^1$H NMR=400 MHz (methanol-$d_4$) δ8.45 (arom, d, 1H), 7.72 (arom, t, 1H), 7.26–7.11 (arom, m, 2H), 4.38 (br s, 1H), 3.57 (MeO, s, 3H), 1.42 (Boc, s, 9H).

C. 4-Acetyl-3-pyridin-2-ylmethyl-piperazine-1,3-dicarboxylic acid 1-tert-butyl ester 3-methyl ester To a stirred solution of the title compound of part 5-B (1.2 g, 3.6 mmol) and diisopropylethylamine (2.5 mL, 14 mmol) in dichloromethane (20 mL) under a nitrogen atmosphere was added acetyl chloride (0.64 mL, 9.0 mmol). The reaction was stirred for about 15 hours, then quenched with saturated aqueous NaHCO$_3$. Additional methylene chloride was added and the mixture was washed twice with saturated NaHCO$_3$, then brine, dried over anhydrous magnesium sulfate, filtered and concentrated in vacuo to give the crude product the title compound of part 5-C (1.2 g, 89%): +APcI MS (M+H)+ 378; $^1$H NMR=400 MHz (CDCl$_3$) δ: 8.48 (arom., s, 1H), 7.54 (arom., m, 1H), 7.13 (arom., m, 2H), 3.69 (MeO, d, 3H), 3.08 (t, 1H), 1.93 (MeCO, d, 3H), 1.42 (BOC, d, 9H).

D. 6,8-Dioxo-8a-pyridin-2-ylmethyl-hexahydro-pyrrolo[1,2-a]pyrazine-2-carboxylic acid tert-butyl ester To a stirred solution of the title compound of part 5-C (2.2 g, 5.8 mmol) in anhydrous tetrahydrofuran (20 mL) cooled to about −78° C. under nitrogen atmosphere was added a 1M solution of lithium bis(trimethylsilyl)amide in tetrahydrofuran (17.5 mL, 17.5 mmol), dropwise. The reaction was stirred at −78° C. for about 1 hour, then the reaction was quenched with methanol and concentrated in vacuo. Ethyl acetate was added, and the mixture was extracted with saturated sodium bicarbonate solution, brine, dried over anhydrous magnesium sulfate, filtered and concentrated in vacuo to give the title compound of part 5-D (1.9 g, 95%): −APcI MS (M−H)− 344; $^1$H NMR=400 MHz (CDCl$_3$) δ: 8.40 (arom., d, 1H), 7.57 (arom., t, 1H), 7.11 (arom., t, 1H), 7.06 (arom., d, 1H), 3.25 (CHHPh, d, 1H), 2.92 (CHHPh, d, 1H), 1.50 (BOC, s, 9H).

E. 8-Methoxy-6-oxo-8a-pyridin-2-ylmethyl-3,4,6,8a-tetrahydro-1H-pyrrolo[1,2-a]pyrazine-2-carboxylic acid tert-butyl ester To a stirred suspension of the title compound of part 5-D (200 mg, 0.58 mmol) in anhydrous ether (2 mL) cooled to about 0° C. under nitrogen atmosphere was added a 1M solution of (trimethylsilyl)diazomethane in hexanes (1.74 mL, 1.74 mmol), dropwise. After about 1 hour, then the reaction was diluted with ethyl acetate the mixture was washed with saturated sodium bicarbonate solution, brine, dried over anhydrous magnesium sulfate, filtered and concentrated in vacuo. Purification by silica gel chromatography using 0–10% methanol/ethyl acetate as eluent afforded the title compound of part 5-E (76 mg, 36%): +APcI MS (M+H)+ 360; $^1$H NMR=400 MHz (CDCl$_3$) δ: 8.42 (arom., d, 1H), 7.50 (arom., t, 1H), 7.08 (arom., t, 1H), 6.89 (arom., d, 1H), 4.84 (COCH=C, s, 1H), 3.79 (CH$_3$O, d, 3H), 3.34 (d, 1H), 1.49 (BOC, s, 9H).

F. 8-Methoxy-8a-pyridin-2-ylmethyl-1,3,4,8a-tetrahydro-2H-pyrrolo[1,2-a]pyrazin-6-one, hydrochloride The title compound of part 5-E (76 mg, 0.21 mmol) was deprotected according to the method described in General Procedure B to give the title compound of part 5-F (60 mg, quantitative): +APcI MS (M+H)+ 260; $^1$H NMR=400 MHz (methanol-$d_4$) δ: 8.79 (arom., d, 1H), 8.57 (arom., t, 1H), 8.02 (arom., t, 1H), 7.82 (arom., d, 1H), 5.09 (COCH=C, s, 1H), 4.43 (dd, 1H), 3.84 (CH$_3$O, d, 1H), 2.98 (td, 1H).

G. {1-[1(R)-Benzyloxymethyl-2-(8-methoxy-6-oxo-8a(R,S)-pyridin-2-ylmethyl-3,4,6,8a-tetrahydro-1H-pyrrolo[1,2- a]pyrazin-2-yl)-2-oxo-ethylcarbamoyl]-1-methyl-ethyl}-carbamic acid tert-butyl ester According to General Procedure A, the title compound of part 5-F (60 mg, 0.88 mmol) was coupled to 3(R)-benzyloxy-2-(2-tert-butoxycarbonylamino-2-methyl-propionyl-amino)-propionic acid (132 mg, 0.35 mmol) and the product was purified by silica gel chromatography using 0–5% methanol/ethyl acetate as eluent to give the title compound of part 5-G (91 mg, 63%) as a 1:1 mixture of diastereomers: +APcI MS (M+H)+ 622; $^1$H NMR=400 MHz (CDCl$_3$) δ: 8.35 (arom., d, 1H), 7.50–6.50 (arom., series of m, 8H), 5.21 (m, 1H), 4.55 (s, 0.5H), 4.46 (PhCH$_2$O, ABq, 1H), 3.80–3.73 (CH$_3$O, m, 3H).

H. 2-Amino-N-[1(R)-benzyloxymethyl-2-(8-methoxy-6-oxo-8a(R,S)-pyridin-2-ylmethyl-3,4,6,8a-tetrahydro-1H-pyrrolo[1,2-a]pyrazin-2-yl)-2-oxo-ethyl]-2-methyl-propionamide, hydrochloride The title compound of part 5-G (91 mg, 0.15 mmol) was deprotected according to the method described in General Procedure B, and the product was triturated with ethyl ether to give the title compound of Example 5 (62 mg, 81%) as a colorless solid: +APcI MS (M+H)$^+$ 522; $^1$H NMR=400 MHz (methanol-d$_4$) δ: 8.80–7.10 (arom., series of m, 9H), 3.80 (CH$_3$O, s, 1.5H), 3.72 (CH$_3$O, s, 1.5H), 2.84 (d, 0.5H), 2.78 (d, 0.5H), 1.58 (CH$_3$O, m, 6H).

EXAMPLE 6

2-Amino-N-{1(R)-benzyloxymethyl-2-[8a(S)-(4-fluoro-benzyl)-6-oxo-8-pyrrolidin-1-yl-3,4,6,8a-tetrahydro-1H-pyrrolo[1,2-a]pyrazin-2-yl]-2-oxo-ethyl}-2-methyl-propionamide, hydrochloride

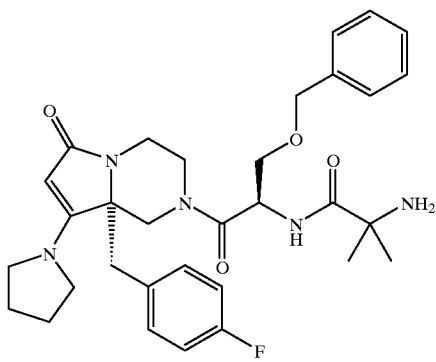

A. 8a-(4-Fluoro-benzyl)-6-oxo-8-pyrrolidin-1-yl-3,4,6,8a-tetrahydro-1H-pyrrolo[1,2-a]pyrazine-2-carboxylic acid tert-butyl ester A solution of the title compound of part 1-D (50 mg, 0.14 mmol) in pyrolidine (0.23 mL) was heated to 120° C. After about 3 days the reaction, which had turned red, was cooled, diluted with ethyl acetate and washed with saturated aqueous sodium bicarbonate and brine, dried over anhydrous magnesium sulfate, and then concentrated in vacuo to give the title compound of part 6-A (48 mg, 83%) as a colorless solid: +APcI MS (M+H)+ 416; $^1$H NMR=400 MHz (CDCl$_3$) δ: 7.02–6.75 (arom, m, 4H), 5.22 (dd, 1h), 4.35 (COCH=C, s, 1H), (1.97 (br s, 4H), 1.49 (BOC, s, 9H).

B. 8a-(4-Fluoro-benzyl)-8-pyrrolidin-1-yl-1,3,4,8a-tetrahydro-2H-pyrrolo[1,2-a]pyrazin-6-one, hydrochloride The title compound of part 6-A (48 mg, 0.12 mmol) was deprotected according to the method described in General Procedure B to give the title compound of part 6-B (46 mg, quantitative): +APcI MS (M+H)$^+$ 316; $^1$H NMR=400 MHz (methanol-d$_4$) δ: 7.10–6.92 (arom., series of m, 4H), 4.39 (br d, 1H), 4.30 (d, 1H), 3.04 (br t, 1H), 2.09 (br s, 4H).

C. (1-{1(R)-Benzyloxymethyl-2-[8a(S)-(4-fluoro-benzyl)-6-oxo-8-pyrrolidin-1-yl-3,4,6,8a-tetrahydro-1H-pyrrolo[1,2-a]pyrazin-2-yl]-2-oxo-ethylcarbamoyl}-1-methyl-ethyl)-carbamic acid tert-butyl ester According to General Procedure A, the title compound of part 6-B (46 mg, 0.15 mmol) was coupled to 3(R)-benzyloxy-2-(2-tert-butoxycarbonylamino-2-methyl-propionyl-amino)propionic acid (67 mg, 0.18 mmol) and the product was purified by silica gel chromatography using 0-1-3% methanol/ethyl acetate as eluent to give the title compound of part 6-C (15 mg, 15%, fractions which contained a nearly 1:1 mixture of the two diastereomers (5 mg), followed by the more polar diastereomer (16 mg, 16%). Title compound of part 6-C: +APcI MS (M+H)+ 678; $^1$H NMR= 400 MHz (CDCl$_3$) δ: 7.35–6.65 (arom., series of m, 9H), 4.48 (PhCH$_2$O, ABq, 2H), 4.37 (COCH=C, s, 1H), 2.70 (d, 1H), 1.98 (s, 4H), 1.46 (CH$_3$, s, 3H), 1.44 (CH$_3$, s, 3H), 1.34 (BOC, s, 9H). For isomer: $^1$H NMR=400 MHz (CDCl$_3$) δ: 7.30–6.58 (arom., series of m, 9H), 4.53 (PhCHHO, d, 1H), 4.45 (PhCHHO, d, 1H), 4.32 (COCH=C, s, 1H), 2.61 (d, 1H), 1.95 (s, 4H), 1.46 (CH$_3$, s, 3H), 1.42 (CH$_3$, s, 3H), 1.40 (BOC, s, 9H).

D. 2-Amino-N-{1(R)-benzyloxymethyl-2-[8a(S)-(4-fluoro-benzyl)-6-oxo-8-pyrrolidin-1-yl-3,4,6,8a-tetrahydro-1H-pyrrolo[1,2-a]pyrazin-2-yl]-2-oxo-ethyl}-2-methyl-propionamide, hydrochloride The title compound of part 6-C (15 mg, 0.022 mmol) was deprotected according to the method described in General Procedure B, and the product was triturated with ethyl ether to give the title compound of Example 6 (11 mg, 86%): +APcI MS (M+H)$^+$ 578; $^1$H NMR=400 MHz (methanol-d$_4$) δ: 7.37–6.87 (arom., series of m, 9H), 4.54 (s, 2H), 2.94 (d, 1H), 2.07 (s, 4H), 1.60 (Me, s, 6H).

EXAMPLE 7

2-Amino-N-[2-(8a(S)-benzyl-6-oxo-3,4,6,8a-tetrahydro-1H-pyrrolo[1,2-a]pyrazin-2-yl)-1(R)-benzyloxymethyl-2-oxo-ethyl]-2-methyl-propionamide, hydrochloride

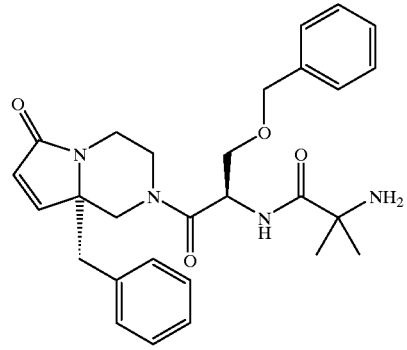

A. 3-Benzyl-3-formyl-piperazine-1-carboxylic acid tert-butyl ester

A solution of the title compound of part 4-B (0.31 g, 0.92 mmol) in CH$_2$Cl$_2$ (4.5 mL) was cooled to −40° C. under a nitrogen atmosphere and a 1.0 M solution of DIBAL in CH$_2$Cl$_2$ (2.8 mL, 2.8 mmol) was added dropwise. After stirring at −40° C. for about 1 h the reaction was quenched with MeOH (1 mL) and water (2 mL). The reaction was warmed, adjusted to Ph 3 with 1 M aqueous hydrochloric acid and then extracted with methylene chloride. The combined extracts were washed with brine, dried over sodium sulfate and concentrated to give the title compound of part 7-A (0.34 g, quantitative) which was carried on without further purification: +APcI MS (M+H)+ 305; 1H NMR=400 MHz (CDCl3) δ: 9.60 (CHO, br m, 1H), 1.40 (BOC, m, 9H).

B. 3-Benzyl-3-(2-methoxycarbonyl-vinyl)-piperazine-1-carboxylic acid tert-butyl ester:

To a THF (1 mL) solution of NaHMDS at 0° C. under a nitrogen atmosphere was added trimethyl phosphonoacetate (0.18 mL, 1.1 mmol), dropwise. After stirring for 1 about hour, a THF (1 mL) solution of the title compound of part 7-A (0.34 mg, 0.92 mmol) was added and the reaction was allowed to warm to room temperature. After stirring for about 16 hours, the product was isolated by extraction from water with EtOAc (2×) and methylene chloride (2×). The combined extracts were washed with brine, dried (MgSO4) and concentrated. The product was then purified by silica gel chromatography using methylene chloride, then 5% MeOH in methylene chloride as eluents to afford a 7:3 E:Z mixture of the title olefins of part 7-B (0.38 g, 81%), where the Z isomer had lactamized: +APcI MS (M+H, ester)+ 361, (M−tBu+H, lactam)+ 273; 1H NMR (400 MHz, CDCl3) δ: 7.30–7.05 (arom, series of m, 5 H), 6.91 (lactam olefin, d, 0.3H), 6.75 (ester olefin, d, 0.7H), 6.09 (lactam olefin, d, 0.3H), 5.88 (ester olefin, d, 0.7H), 3.71 (ester Me, s, 2.1 H), 1.47 (BOC, s, 9H).

C. 8a-Benzyl-1,3,4,8a-tetrahydro-2H-pyrrolo[1,2-a]pyrazin-6-one, hydrochloride

A solution of the title compounds of part 7-B (200 mg, 0.55 mmol) in methanol (5 mL) under a nitrogen atmosphere was heated to reflux in the presence of solid potassium carbonate. After about 16 hours the reaction was concentrated in vacuo, redissolved in methylene chloride and washed with saturated aqueous ammonium chloride, the organic layer was then dried over anhydrous sodium sulfate and concentrated in vacuo to give the crude, protected amine (97 mg, 50%) as a thick, brown oil.

A portion of the amine (15 mg) was deprotected according to the method described in General Procedure B to give the title compound of part 7-C (8 mg, 77%): +APcI MS (M+H)+ 229; 1H NMR=400 MHz (methanol-d4) δ: 7.40–7.15 (arom., series of m, 5H), 7.05 (d, 1H), 6.00 (d, 1H), 3.83 (d,1H).

D. {1-[2-(8a-Benzyl-6-oxo-3,4,6,8a-tetrahydro-1H-pyrrolo[1,2-a]pyrazin-2-yl)-1-benzyloxymethyl-2-oxo-ethylcarbamoyl]-1-methyl-ethyl}-carbamic acid tert-butyl ester According to General Procedure A, the title compound of part 7-C (8 mg, 0.035 mmol) was coupled to 3(R)-benzyloxy-2-(2-tert-butoxycarbonylamino-2-methyl-propionyl-amino)-propionic acid (19 mg, 0.053 mmol) and the product was purified by silica gel chromatography using 0–10% methanol/ethyl acetate as eluent to give the title compound of part 7-D (1.8 mg, 21%) followed by the more polar diastereomer (2.3 mg, 26%). Title compound of part 7-D: +APcI MS (M−Boc+H)+ 591; 1H NMR=400 MHz (CDCl3) δ: 7.35–6.70 (series of m, 11H), 6.05 (br s, 1H), 5.09 (br m, 1H). For isomer: 1H NMR=400 MHz (CDCl3) δ: 7.20–6.90 (arom., series of m, 10H), 6.86 (COCH=CH, d, 1H), 6.05 (COCH=CH, d, 1H), 5.24 (M, 1H), 4.55 (d, 1H), 2.65 (d, 1H), 1.41 (BOC, s, 9H).

E. 2-Amino-N-[2-(8a(S)-benzyl-6-oxo-3,4,6,8a-tetrahydro-1H-pyrrolo[1,2-a]pyrazin-2-yl)-1(R)-benzyloxymethyl-2-oxo-ethyl]-2-methyl-propionamide, hydrochloride The title compound of part 6-C (1.8 mg, 0.003 mmol) was deprotected according to the method described in General Procedure B, and the product was triturated with ethyl ether to give the title compound of Example 6 (1.5 mg, quantitative): +APcI MS (M+H)+ 591; 1H NMR=400 MHz (methanol-d4) δ: 7.40–7.10 (arom., series of m, 10H), 7.06 (COCH=CH, d, 1H), 6.00 (COCH=CH, d, 1H), 4.55 (s, 2H), 3.04 (d, 1H), 2.42 (d, 1H), 1.59 (Me, s, 3H), 1.55 (Me, s, 3H).

EXAMPLE 8

2-Amino-N{1(R)-benzyloxymethyl-2-[8a(S)-(4-fluoro-benzyl)-8-methoxy-7-methyl-6-oxo-3,4,6,8a-tetrahydro-1H-pyrrolo[1,2-a]pyrazin-2-yl]-2-oxo-ethyl}-2-methyl-propionamide, hydrochloride

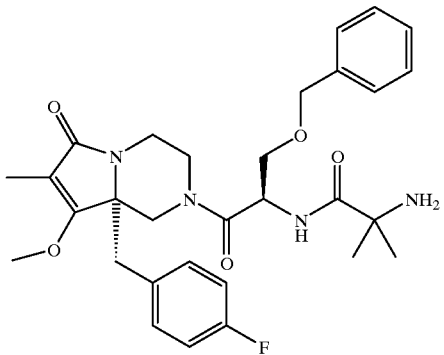

A. 8a-(4-Fluoro-benzyl)-8-methoxy-7-methyl-6-oxo-3,4,6,8a-tetrahydro-1H-pyrrolo[1,2-a]pyrazine-2-carboxylic acid tert-butyl ester:

To a DMSO (2 mL) solution of compound 1-D was added NaH (60% dispersion in mineral oil, 33 mg, 0.83 mmol). After stirring about 1 hour, methyl iodide was added (0.017 mL, 0.28 mmol), the mixture was stirred for 1 hour, and then an additional portion of methyl iodide (0.017 mL, 0.28 mmol) was added. After stirring 3 days, the reaction mixture was extracted from saturated aqueous sodium bicarbonate with EtOAc, and the combined extracts washed with brine, dried (MgSO4) and concentrated. Purification by silica gel chromatography employing hexanes, then 1:1 EtOAc/hexanes as eluents afforded the title compound of part 8-A (9 mg, 14%): +APcI MS (M+H)+ 391; 1H NMR (400 MHz, CDCl3) δ: 6.95–6.83 (arom, m, 4 H), 4.21 (dd, 1H), 3.99 (MeO, s, 3H), 1.76 (Me, s, 3H), 1.50 (BOC, s, 9H).

B. 8a-(4-Fluoro-benzyl)-8-methoxy-7-methyl-1,3,4,8a-tetrahydro-2H-pyrrolo[1,2-a]pyrazin-6-one, hydrochloride The title compound of part 8-A (9 mg, 0.023 mmol) was deprotected according to the method described in General Procedure B to give the title compound of part 8-B (7 mg, 93%): +APcI MS (M+H)+ 291; 1H NMR=400 MHz (methanol-d4) δ: 7.18–6.93 (arom., series of m, 4H), 4.36 (dd, 1H), 4.10 (MeO, s, 3H), 3.70 (d, 1H), 1.73 (Me, s, 3H).

C. (1-{1(R)-Benzyloxymethyl-2-[8a(S)-(4-fluoro-benzyl)-8-methoxy-7-methyl-6-oxo-3,4,6,8a-tetrahydro-1H-pyrrolo[1,2-a]pyrazin-2-yl]-2-oxo-ethylcarbamoyl}-1-methyl-ethyl)-carbamic acid tert-butyl ester According to General Procedure A, the title compound of part 8-B (8 mg, 0.023 mmol) was coupled to 3(R)-benzyloxy-2-(2-tert-butoxycarbonylamino-2-methyl-propionyl-amino)-propionic acid (11 mg, 0.028 mmol) and the product was purified by silica gel chromatography using 20–80% ethyl acetate/hexanes as eluent to give the title compound of part 8-C (2 mg, 13%), fractions which contained a mixture of the two diastereomers (6 mg, 40%), followed by the more polar diastereomer (3 mg, 20%). Title compound of part 8-C: +APcI MS (M+H)+ 653, (M−Boc+H)+ 553; 1H NMR=400 MHz (CDCl3) δ: 7.35–6.65 (series of m, 9H), 5.15 (q, 1H), 4.47 (PhCH2O, Abq, 2H), 3.98 (MeO, s, 3H). For isomer: 1H NMR=400 MHz (CDCl3) δ: 7.70–6.58 (arom., series of m, 10H), 5.20 (M, 1H), 4.54 (PhCHHO, ½ Abq, 1H), 4.44 (PhCHHO, ½ Abq, 1H), 3.93 (MeO, s, 3H).

D. 2-Amino-N-1(R)-benzyloxymethyl-2-[8a(S)-(4-fluoro-benzyl)-8-methoxy-7-methyl-6-oxo-3,4,6,8a-tetrahydro-1H-pyrrolo[1,2-a]pyrazin-2-yl]-2-oxo-ethyl}-2-methyl-propionamide, hydrochloride The title compound of part 8-C (2 mg, 0.003 mmol) was deprotected according to the method described in General Procedure C, and the product was triturated with ethyl ether to give the title compound of Example 8 (2 mg, quantitative): +APcI MS (M+H)⁺ 553; ¹H NMR=400 MHz (methanol-$d_4$) δ: 7.40–6.80 (arom., series of m, 9H), 5.13 (m, 1H), 4.54 (PhC$\underline{H}_2$O, s, 2H), 4.10 (MeO, s, 3H), 3.09 (d, 1H), 2.61 (d, 1H), 1.78 (Me, s, 3H), 1.59 (Me, s, 6H).

TABLES

The following abbreviations and notations are used in the Tables below.

Abbreviation:

Me—methyl
Et—ethyl
Ph—phenyl
Pyr—pyridyl
Pr—cyclopropyl

EXAMPLES 9–17

The compounds of Examples 9–17 were synthesized in a manner analogous to procedures described for Examples 5–8 using the appropriate starting materials.

| Example # | X | R¹ | R² | R²ᴬ | isomer | MSᴬ |
|---|---|---|---|---|---|---|
| 9 | O | CH₂-4-F—Ph | Me | MeO | d2 | 553 |
| 10 | O | CH₂-4-F—Ph | H | MeO | d1 | 539 |
| 11 | O | CH₂-4-F—Ph | H | MeO | d2 | 539 |
| 12 | O | CH₂-4-F—Ph | H | (CH₂)₄N | d2 | 578 |
| 13 | O | CH₂-4-F—Ph | H | O(CH₂CH₂)₂N | d1 | 594 |
| 14 | O | CH₂-4-F—Ph | H | O(CH₂CH₂)₂N | d2 | 594 |
| 15 | O | CH₂Ph | H | H | d2 | 491 |
| 16 | O | CH₂-2-Pyr | H | MeO | d1 | 522 |
| 17 | O | CH₂-2-Pyr | H | MeO | d2 | 522 |

ᴬ= Mass Spec. Method is ⁺APcI

EXAMPLES 9–17

The compounds of Examples 18–45 were synthesized in a manner analogous to procedures described for Examples 1–4 using the appropriate starting materials.

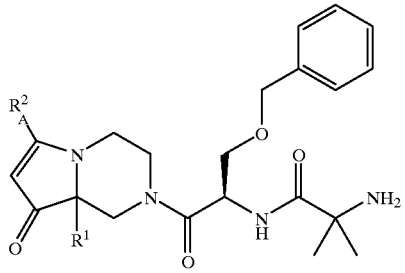

| Example # | R¹ | R²ᴬ | isomer | MSᴬ |
|---|---|---|---|---|
| 18 | CH₂-4-F—Ph | MeS | d2 | 555 |
| 19 | CH₂-4-F—Ph | (CH₂)₄N | d2 | 578 |
| 20 | CH₂-4-F—Ph | Me₂N | d1 | 552 |
| 21 | CH₂-4-F—Ph | Me₂N | d2 | 552 |
| 22 | CH₂-4-F—Ph | H | d2 | 509 |
| 23 | CH₂-4-F—Ph | O(CH₂CH₂)₂N | d1 | 594 |
| 24 | CH₂-4-F—Ph | O(CH₂CH₂)₂N | d2 | 594 |
| 25 | CH₂Ph | (CH₂)₄N | d1 | 560 |
| 26 | CH₂Ph | (CH₂)₄N | d2 | 560 |
| 27 | CH₂Ph | H | d1 | 491 |
| 28 | CH₂Ph | H | d2 | 491 |
| 29 | CH₂Ph | Me | d2 | 505 |
| 30 | CH₂-2-Pyr | Me | d1,2 | 506 |
| 31 | CH₂Ph | Et | d1 | 519 |
| 32 | CH₂Ph | Et | d2 | 519 |
| 33 | CH₂-2-Pyr | Me | d1 | 506 |
| 34 | CH₂-2-Pyr | 2-Pyr | d1,2 | 569 |
| 35 | CH₂-2-Pyr | t-Bu | d1,2 | 548 |
| 36 | CH₂-2-Pyr | Et | d1,2 | 520 |
| 37 | CH₂Ph | i-Pr | d1 | 533 |
| 38 | CH₂Ph | i-Pr | d2 | 533 |
| 39 | CH₂Ph | t-Bu | d1 | 547 |
| 40 | CH₂Ph | t-Bu | d2 | 547 |
| 41 | CH₂-2-Pyr | i-Pr | d1,2 | 534 |
| 42 | CH₂Ph | 2-Pyr | d1 | 568 |
| 43 | CH₂Ph | 2-Pyr | d2 | 568 |
| 44 | Me | 2-Pyr | d1,2 | 492 |
| 45 | Me | Ph | d1,2 | 491 |

ᴬ= Mass Spec. Method is ⁺APcI

What is claimed is:
1. A compound of the Formula

I or a pharmaceutically acceptable salt or prodrug thereof, wherein:

HET is a heterocyclic moiety selected from the group consisting of

-continued

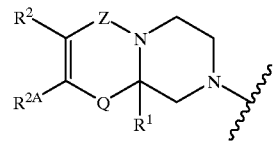

$R^2$ is selected from the group consisting of hydrogen, fluoro, and $(C_1-C_5)$alkyl optionally substituted with 1–5 halo groups;

$R^{2A}$ is selected from the group consisting of hydrogen, $SX^6$, $OX^6$, $-N(X^6)(X^6)$, $(C_1-C_8)$alkyl, $-(C_0-C_3)$alkyl-$(C_1-C_7)$cycloalkyl, and $-(C_0-C_3)$alkyl-$A^1$, where the alkyl groups and the cycloalkyl groups are optionally substituted with hydroxy, thio, $C(O)OX^6$, $C(O)N(X^6)(X^6)$, $SO_2N(X^6)(X^6)$, $S(O)_m(C_1-C_6)$alkyl, $C(O)A^1$, $C(O)(X^6)$, CN or 1–5 halo groups;

Q is is a covalent bond

Z is C=O, C=S or $S(O)_2$;

$R^1$ is hydrogen, $-CN$, $-(CH_2)_qN(X^6)C(O)X^6$, $-(CH_2)_qN(X^6)C(O)(CH_2)_t-A^1$, $-(CH_2)_qN(X^6)S(O)_2(CH_2)_tA^1$, $-(CH_2)_qN(X^6)S(O)_2X^6$, $-(CH_2)_qN(X^6)C(O)N(X^6)(CH_2)_t-A^1$, $-(CH_2)_qN(X^6)C(O)N(X^6)(X^6)$, $-(CH_2)_qC(O)N(X^6)(X^6)$, $-(CH_2)_qC(O)N(X^6)(CH_2)_tA^1$, $-(CH_2)_qC(O)OX^6$, $-(CH_2)_qC(O)O(CH_2)_t-A^1$, $-(CH_2)_qOX^6$, $-(CH_2)_qOC(O)X^6$, $-(CH_2)_qOC(O)(CH_2)_t-A^1$, $-(CH_2)_qOC(O)N(X^6)(CH_2)_t-A^1$, $-(CH_2)_qOC(O)N(X^6)(X^6)$, $-(CH_2)_qC(O)X^6$, $-(CH_2)_qC(O)(CH_2)_t-A^1$, $-(CH_2)_qN(X^6)C(O)OX^6$, $-(CH_2)_qN(X^6)S(O)_2N(X^6)(X^6)$, $-(CH_2)_qS(O)_mX^6$, $-(CH_2)_qS(O)_m(CH_2)_t-A^1$, $-(C_1-C_{10})$alkyl, $-(CH_2)_t-A^1$, $-(CH_2)_q-(C_3-C_7)$cycloalkyl, $-(CH_2)_q-Y^1-(C_1-C_6)$alkyl, $-(CH_2)_q-Y^1-(CH_2)_t-A^1$ or $-(CH_2)_q-Y^1-(CH_2)_t-(C_3-C_7)$cycloalkyl;

wherein the alkyl and cycloalkyl groups in the definition of $R^1$ are optionally independently substituted with $(C_1-C_4)$alkyl, hydroxy, $(C_1-C_4)$alkoxy, carboxyl, $-CONH_2$, $-S(O)_m(C_1-C_6)$alkyl, $-CO_2(C_1-C_4)$alkyl ester, 1H-tetrazol-5-yl or 1, 2 or 3 fluoro groups;

$Y^1$ is O, $S(O)_m$, $-C(O)NX^6-$, $-CH=CH-$, $-C\equiv C-$, $-N(X^6)C(O)-$, $-C(O)NX^6-$, $-C(O)O-$, $-OC(O)N(X^6)-$ or $-OC(O)-$;

q is 0, 1, 2, 3 or 4, with the proviso that q cannot be 0 when $(CH_2)_q$ is attached to N or O;

t is 0, 1, 2 or 3;

m is 1 or 2;

$R^3$ is selected from the group consisting of $A^1$, $(C_1-C_{10})$alkyl, $-(C_1-C_6)$alkyl-$A^1$, $-(C_1-C_6)$alkyl-$(C_3-C_7)$cycloalkyl, $-(C_1-C_5)$alkyl-$X^1-(C_1-C_5)$alkyl, $-(C_1-C_5)$alkyl-$X^1-(C_0-C_5)$alkyl-$A^1$ and $-(C_1-C_5)$alkyl-$X^1-(C_1-C_5)$alkyl-$(C_3-C_7)$cycloalkyl;

where the alkyl groups in the definition of $R^3$ are optionally substituted with $-S(O)_m(C_1-C_6)$alkyl, $-C(O)OX^3$, 1, 2, 3, 4 or 5 independently selected halo groups or 1, 2 or 3 independently selected $-OX^3$ groups;

$A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, on one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, $-OX^6$, $-C(O)N(X^6)(X^6)$, $-C(O)OX^6$, oxo, $(C_1-C_6)$alkyl, nitro, cyano, benzyl, $-S(O)_m(C_1-C_6)$alkyl, 1H-tetrazol-5-yl, phenyl, phenoxy, phenylalkyloxy, halophenyl, methylenedioxy, $-N(X^6)(X^6)$, $-N(X^6)C(O)(X^6)$, $-S(O)_2N(X^6)(X^6)$, $-N(X^6)S(O)_2$-phenyl, $-N(X^6)S(O)_2X^6$, $-CONX^{11}X^{12}$, $-S(O)_2NX^{11}X^{12}$, $-NX^6S(O)_2X^{12}$, $-NX^6CONX^{11}X^{12}$, $-NX^6S(O)_2NX^{11}X^{12}$, $-NX^6C(O)X^{12}$, imidazolyl, thiazolyl and tetrazolyl, provided that if $A^1$ is optionally substituted with methylenedioxy then it can only be substituted with one methylenedioxy;

where $X^{11}$ is hydrogen or optionally substituted $(C_1-C_6)$alkyl;

the optionally substituted $(C_1-C_6)$alkyl defined for $X^{11}$ is optionally independently substituted with phenyl, phenoxy, $(C_1-C_6)$alkoxycarbonyl, $-S(O)_m(C_1-C_6)$alkyl, 1 to 5 halo groups, 1 to 3 hydroxy groups, 1 to 3 $(C_1-C_{10})$alkanoyloxy groups or 1 to 3 $(C_1-C_6)$alkoxy groups;

$X^{12}$ is hydrogen, $(C_1-C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, $CH_3$, $OCH_3$, $OCF_3$ and $CF_3$;

or $X^{11}$ and $X^{12}$ are taken together to form $-(CH_2)_r-L^1-(CH_2)_r-$;

$L^1$ is $C(X^2)(X^2)$, O, $S(O)_m$ or $N(X^2)$;

r for each occurrence is independently 1, 2 or 3;

$X^1$ is O, $S(O)_m$, $-N(X^2)C(O)-$, $-C(O)N(X^2)-$, $-OC(O)-$, $-C(O)O-$, $-CX^2=CX^2-$, $-N(X^2)C(O)O$, $-OC(O)N(X^2)-$ or $-C\equiv C-$;

$X^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with $-S(O)_m(C_1-C_6)$alkyl, $-C(O)OX^3$, 1 to 5 halo groups or 1–3 $OX^3$ groups;

$X^3$ for each occurrence is independently H or (C1–C6) alkyl $X^6$ for each occurrence is independently hydrogen, optionally substituted $(C_1-C_6)$alkyl, $(C_2-C_6)$ halogenated alkyl, optionally substituted $(C_3-C_7)$ cycloalkyl, $(C_3-C_7)$-halogenated cycloalkyl, where optionally substituted $(C_1-C_6)$alkyl and optionally substituted $(C_3-C_7)$cycloalkyl in the definition of $X^6$ is optionally independently mono- or di-substituted with $(C_1-C_4)$alkyl, hydroxy, $(C_1-C_4)$alkoxy, carboxyl, $CONH_2$, $S(O)_m(C_1-C_6)$alkyl, carboxylate $(C_1-C_4)$ alkyl ester or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$ as a ring member;

$X^7$ is hydrogen or $(C_1-C_6)$alkyl optionally substituted with hydroxy;

m for each occurrence is independently 0, 1 or 2;

$R^4$ is hydrogen or methyl;

$X^4$ is hydrogen;

$R^6$ is

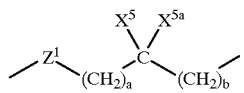

where $Z^1$ is a bond and a is 0 or 1; $X^5$ and $X^{5a}$ are each independently selected from the group consisting of hydrogen, $CF_3$, phenyl and optionally substituted $(C_1-C_6)$ alkyl;

where the optionally substituted $(C_1-C_6)$alkyl in the definition of $X^5$ and $X^{5a}$ is optionally substituted with $OX^2$, imidazolyl, phenyl, indolyl, p-hydroxyphenyl, $(C_5-C_7)$ cycloalkyl, $—S(O)_m(C_1-C_6)$alkyl, $—N(X^2)(X^2)$ or $—C(O)$ $N(X^2)(X^2)$;

$R^7$ is hydrogen or $(C_1-C_3)$alkyl;

or $X^5$ and $R^7$ are taken together and form a $(C_1-C_5)$ alkylene bridge; and $R^8$ is hydrogen or $(C_1-C_3)$alkyl optionally substituted with one or two hydroxy groups; with the proviso that: $X^6$ and $X^{12}$ cannot be hydrogen when attached to $C(O)$ or $S(O)_2$ in the form $C(O)X^6$, $C(O)X^{12}$, $S(O)_2X^6$ or $S(O)_2X^{12}$.

2. A compound, a salt or a prodrug according to claim 1 wherein b is O; $X^5$ and $X^{5a}$ are each independently selected from the group consisting of hydrogen, $(C_1-C_3)$alkyl and hydroxy$(C_1-C_3)$alkyl; and $R^3$ is selected from the group consisting of thienyl-$CH_2$— O—$CH_2$—, pyridyl-$CH_2$—O—$CH_2$—, thiazolyl-$CH_2$—O—$CH_2$—, 1-indolyl-$CH_2$—, 2-indolyl-$CH_2$—, 3-indolyl-$CH_2$—, 1-naphthyl-$CH_2$, 2-naphthyl-$CH_2$—, 1-benzimidazolyl-$CH_2$—, 2-benzimidazolyl-$CH_2$—, phenyl-$(C_1-C_4)$alkyl, 2-pyridyl-$(C_1-C_4)$alkyl—, 3-pyridyl-$(C_1-C_4)$alkyl-, 4-pyridyl-$(C_1-C_4)$alkyl-, phenyl-$CH_2$—S—$CH_2$—, thienyl-$(C_1-C_4)$alkyl-, phenyl-$(C_0-C_3)$alkyl-O—$CH_2$—, phenyl-$CH_2$—O-phenyl-$CH_2$—, phenyl-O—$CH_2$—$CH_2$— and 3-benzothienyl-$CH_2$—;

where the aryl portion(s) of the groups defined for $R^3$ are each optionally substituted with one to three substituents, each substituent being independently selected from the group consisting of methylenedioxy, F, Cl, $CH_3$, $OCH_3$, $OCF_3$, $OCF_2H$ and $CF_3$.

3. A compound, a salt or a prodrug according to claim 2 wherein:

$R^4$ is hydrogen; a is 0;

$X^5$ and $X^{5a}$ are each independently selected from the group consisting of hydrogen, methyl or hydroxymethyl, provided that when $X^5$ is hydrogen then $X^{5a}$ is not hydrogen;

$R^7$ and $R^8$ are each hydrogen; and $R^3$ is selected from the group consisting of 3-indolyl-$CH_2$—, 1-naphthyl-$CH_2$—, 2-naphthyl-$CH_2$—, phenyl-$(C_1-C_4)$alkyl-, 2-pyridyl-$(C_1-C_4)$alkyl-, 3-pyridyl-$(C_1-C_4)$alkyl-, 4-pyridyl-$(C_1-C_4)$alkyl-, phenyl-$CH_2$—S—$CH_2$—, thienyl-$(C_2-C_4)$alkyl-, phenyl-$(C_0-C_3)$alkyl-O—$CH_2$—, 3-benzothienyl-$CH_2$—, thienyl-$CH_2$—O—$CH_2$—, thiazolyl-$CH_2$—O—$CH_2$—, pyridyl-$CH_2$—O—$CH_2$— and phenyl-O—$CH_2$—$CH_2$—;

where the aryl portion(s) of the groups defined for $R^3$ are each optionally substituted with one to three substituents, each substituent being independently selected from the group consisting of methylenedioxy, F, Cl, $CH_3$, $OCH_3$, $OCF_3$, $OCF_2H$ and $CF_3$.

4. A compound, a salt or a prodrug according to claim 3 wherein:

$R^1$ is $—(CH_2)_t—A^1$, $—(CH_2)_q—(C_3-C_7)$cycloalkyl or $(C_1-C_{10})$alkyl;

$A^1$ in the definition of $R^1$ is phenyl, pyridyl, thiazolyl or thienyl, optionally substituted with one to three substituents, each substituent being independently selected from the group consisting of F, Cl, $CH_3$, $OCH_3$, $OCF_2H$, $OCF_3$ and $CF_3$;

the cycloalkyl and alkyl groups in the definition of $R^1$ are optionally substituted with $(C_1-C_4)$alkyl, hydroxy, $(C_1-C_4)$alkoxy or 1 to 3 fluoro atoms;

q is 1 or 2; t is 1 or 2;

$R^3$ is phenyl-$CH_2$—O—$CH_2$—, phenyl-$CH_2$—S—$CH_2$—, pyridyl-$CH_2$—O—$CH_2$—, thienyl-$CH_2$—O—$CH_2$—, thiazolyl-$CH_2$—O—$CH_2$—, phenyl-$(CH_2)_3$— or 3-indolyl-$CH_2$—;

where the carbon atom bearing the substituent $R^3$ is of the (R)-configuration;

where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$; and $X^5$ and $X^{5a}$ are each methyl.

5. A compound, a salt or a prodrug according to claim 4 wherein HET is

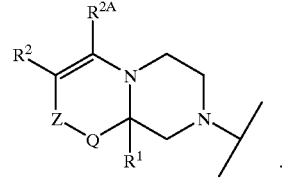

6. A compound, a salt or a prodrug according to claim 5 wherein Z is C=O; Q is a covalent bond.

7. A compound, a salt or a prodrug according to claim 6 wherein:

$R^2$ is hydrogen or $(C_1-C_3)$alkyl where the alkyl is optionally substituted with 1–3 fluoro groups;

$R^{2A}$ is $—SX^6$;

$X^6$ is $(C_1-C_3)$alkyl or $(C_3-C_6)$ cycloalkyl, where the alkyl and cycloalkyl may be optionally substituted with one to three halogens.

8. A compound, a salt or a prodrug according to claim 7 wherein:

$R^1$ is $—CH_2—A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and $R^3$ is selected form the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

9. A compound, a salt or a prodrug according to claim 8 where the compound is the 8a(R,S),1(R) diastereomeric mixture, the 8a(R),1(R) diastereomer or the 8a(S),1(R) diastereomer of 2-amino-N-{1(R)-benzyloxymethyl-2-[8a-(4-fluoro-benzyl)-6-methylsulfanyl-8-oxo-3,4,8,8a-tetrahydro-1H-pyrrolo[1,2-a]pyrazin-2-yl]-2-oxo-ethyl}-2-methyl-propionamide.

10. A compound, a salt or a prodrug according to claim 8 wherein:
$R^2$ is hydrogen or $(C_1-C_3)$alkyl where the alkyl is optionally substituted with 1–3 fluoro groups;
$R^{2A}$ is —$N(X^6)(X^6)$;
$X^6$ for each occurrence is independently hydrogen, optionally substituted $(C_1-C_3)$alkyl, $(C_2-C_3)$ fluoronated alkyl, optionally substituted $(C_3-C_6)$ cycloalkyl, $(C_3-C_6)$fluorinated cycloalkyl, where when there are two $X^6$ groups on one atom and both $X^6$ are independently $(C_1-C_3)$alkyl, the two $(C_1-C_3)$alkyl groups may be optionally joined and, together with the atom to which the two $X^6$ groups are attached, form a 4- to 6-membered ring optionally having oxygen as a ring member.

11. A compound, a salt or a prodrug according to claim 10 wherein:
$R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and
$R^3$ is selected form the group consisting of 3-indolyl-$CH_2$—, phenyl—$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

12. A compound, a salt or a prodrug according to claim 11 where the compound is the 8a(R,S),1(R) diastereomeric mixture, the 8a(R),1(R) diastereomer or the 8a(S),1(R) diastereomer of the compound selected from the group consisting of 2-amino-N-{1(R)-benzyloxymethyl-2-[8a-(4-fluoro-benzyl)-8-oxo-6-pyrrolidin-1-yl-3,4,8,8a-tetrahydro-1H-pyrrolo[1,2-a]pyrazin-2-yl]-2-oxo-ethyl}-2-methyl-propionamide or 2-amino-N-{1(R)-benzyloxymethyl-2-[8a-(4-fluoro-benzyl)-6-morpholin-4-yl-8-oxo-3,4,8,8a-tetrahydro-1H-pyrrolo[1,2-a]pyrazin-2-yl]-2-oxo-ethyl}-2-methyl-propionamide.

13. A compound, a salt or a prodrug according to claim 6 wherein:
$R^2$ is hydrogen or $(C_1-C_3)$alkyl where the alkyl is optionally substituted with 1–3 fluoro groups;
$R^{2A}$ is hydrogen, -$(C_1-C_4)$alkyl, -$(C_0-C_2)$alkyl-$(C_1-C_6)$ cycloalkyl, -$(C_0-C_2)$alkyl-$A^1$ where the alkyl groups are optionally substituted with 1–3 fluoro groups;
$A^1$ is phenyl, pyridyl or thiazolyl optionally substituted with one to two substituents, each substituent being independently selected from the group consisting of F, Cl, $CH_3$, $OCF_2H$, $OCF_3$, and $CF_3$.

14. A compound, a salt or a prodrug according to claim 13 wherein:
$R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and
$R^3$ is selected form the group consisting of 3-indolyl-$CH_2$—, phenyl—$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

15. A compound, a salt or a prodrug according to claim 14 where the compound is the 8a(R,S),1(R) diastereomeric mixture, the 8a(R),1(R) diastereomer or the 8a(S),1(R) diastereomer of the compound selected from the group consisting of 2-amino-N-{1(R)-benzyloxymethyl-2-[8a-(4-fluoro-benzyl)-8-oxo-3,4,8,8a-tetrahydro-1H-pyrrolo[1,2-a]pyrazin-2-yl]-2-oxo-ethyl}-2-methyl-propionamide, 2-amino-N-[1(R)-benzyloxymethyl-2-oxo-2-(8-oxo-6-pyridin-2-yl-8a-pyridin-2-ylmethyl-3,4,8,8a-tetrahydro-1H-pyrrolo[1,2-a]pyrazin-2-yl)-ethyl]-2-methyl-propionamide, or 2-amino-N-[2-(8a-benzyl-6-ethyl-8-oxo-3,4,8,8a-tetrahydro-1H-pyrrolo[1,2-a]pyrazin-2-yl)-1(R)-benzyloxymethyl-2-oxo-ethyl]-2-methyl-propionamide.

16. A compound, a salt or a prodrug according to claim 4 wherein HET is

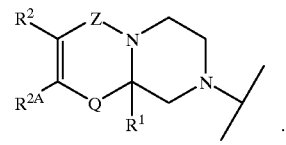

17. A compound, a salt or a prodrug according to claim 16 wherein Z is C=O; Q is a covalent bond.

18. A compound, a salt or a prodrug according to claim 17 wherein:
$R^2$ is hydrogen or $(C_1-C_3)$alkyl where the alkyl is optionally substituted with 1–3 fluoro groups;
$R^{2A}$ is —$OX^6$;
$X^6$ is $(C_1-C_3)$alkyl or $(C_3-C_6)$ cycloalkyl, where the alkyl and cycloalkyl may be optionally substituted with one to three halogens.

19. A compound, a salt or a prodrug according to claim 18 wherein:
$R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and
$R^3$ is selected form the group consisting of 3-indolyl-$CH_2$—, phenyl—$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

20. A compound, a salt or a prodrug according to claim 19 where the compound is the 8a(R,S),1(R) diastereomeric mixture, the 8a(R),1(R) diastereomer or the 8a(S),1(R) diastereomer of the compound selected from the group consisting of 2-amino-N-[1(R)-benzyloxymethyl-2-(8-methoxy-6-oxo-8a-pyridin-2-ylmethyl-3,4,6,8a-tetrahydro-1H-pyrrolo[1,2-a]pyrazin-2-yl)-2-oxo-ethyl]-2-methyl-propionamide, 2-amino-N-{1(R)-benzyloxymethyl-2-[8a-(4-fluoro-benzyl)-8-methoxy-6-oxo-3,4,6,8a-tetrahydro-1H-pyrrolo[1,2-a]pyrazin-2-yl]-2-oxo-ethyl}-2-methyl-propionamide or 2-amino-N-{1(R)-benzyloxymethyl-2-[8a-(4-fluorobenzyl)-8-methoxy-7-methyl-6-oxo-3, 4,6,8a-tetrahydro-1H-pyrrolo[1,2-a]pyrazin-2-yl]-2-oxo-ethyl}-2-methyl-propionamide.

21. A compound, a salt or a prodrug according to claim 17 wherein:
$R^2$ is hydrogen, -($C_1$-$C_4$)alkyl, -($C_0$-$C_2$)alkyl-($C_1$-$C_6$) cycloalkyl, -($C_0$-$C_2$)alkyl-$A^1$ where the alkyl groups are optionally substituted with 1–3 fluoro groups;
$A^1$ is phenyl, pyridyl or thiazolyl optionally substituted with one to two substituents, each substituent being independently selected from the group consisting of F, Cl, $CH_3$, $OCF_2H$, $OCF_3$, and $CF_3$;
$R^{2A}$ is —N($X^6$)($X^6$);
$X^6$ for each occurrence is independently hydrogen, optionally substituted ($C_1$–$C_3$)alkyl, ($C_2$–$C_3$) fluoronated alkyl, optionally substituted ($C_3$–$C_6$) cycloalkyl, ($C_3$–$C_6$)fluoronated cycloalkyl, where when there are two $X^6$ groups on one atom and both $X^6$ are independently ($C_1$–$C_3$)alkyl, the two ($C_1$–$C_3$)alkyl groups may be optionally joined and, together with the atom to which the two $X^6$ groups are attached, form a 4- to 6-membered ring optionally having oxygen as a ring member.

22. A compound, a salt or a prodrug according to claim 2 wherein:
$R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and
$R^3$ is selected form the group consisting of 3-indolyl-$CH_2$—, phenyl—($CH_2$)$_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

23. A compound, a salt or a prodrug according to claim 22 where the compound is the 8a(R,S),1(R) diastereomeric mixture, the 8a(R),1(R) diastereomer or the 8a(S),1(R) diastereomer of the compound selected from the group consisting of 2-amino-N-{1(R)-benzyloxymethyl-2-[8a-(4-fluoro-benzyl)-6-oxo-8-pyrrolidin-1-yl-3, 4,6,8a-tetrahydro-1H-pyrrolo[1,2-a]pyrazin-2-yl]-2-oxo-ethyl}-2-methyl-propionamide or 2-amino-N-{1(R)-benzyloxymethyl-2-[8a-(4-fluoro-benzyl)-8-morpholin-4-yl-6-oxo-3, 4,6,8a-tetrahydro-1H-pyrrolo[1,2-a]pyrazin-2-yl]-2-oxo-ethyl}-2-methyl-propionamide.

24. A compound, a salt or a prodrug according to claim 17 wherein:
$R^2$ is hydrogen or ($C_1$–$C_3$)alkyl where the alkyl is optionally substituted with 1–3 fluoro groups;
$R^{2A}$ is hydrogen, -($C_1$-$C_4$)alkyl, —($C_0$-$C_2$)alkyl-($C_1$-$C_6$) cycloalkyl, -($C_0$-$C_2$)alkyl-$A^1$ where the alkyl groups are optionally substituted with 1–3 fluoro groups;
$A^1$ is phenyl, pyridyl or thiazolyl optionally substituted with one to two substituents, each substituent being independently selected from the group consisting of F, Cl, $CH_3$, $OCF_2H$, $OCF_3$, and $CF_3$.

25. A compound, a salt or a prodrug according to claim 24 wherein:
$R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and
$R^3$ is selected form the group consisting of 3-indolyl-$CH_2$—, phenyl-($CH_2$)$_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

26. A compound, a salt or a prodrug according to claim 25 where the compound is the 8a(R,S),1(R) diastereomeric mixture, the 8a(R),1(R) diastereomer or the 8a(S),1(R) diastereomer of 2-amino-N-[2-(8a-benzyl-6-oxo-3,4,6,8a-tetrahydro-1H-pyrrolo[1,2-a]pyrazin-2-yl)-1(R)-benzyloxymethyl-2-oxo-ethyl]-2-methyl-propionamide.

27. A method for increasing levels of endogenous growth hormone in a human or other animal which comprises administering to such human or animal a therapeutically effective amount of a compound, a salt or a prodrug according to claim 1.

28. A pharmaceutical composition which comprises a pharmaceutically acceptable carrier and an effective amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

29. A pharmaceutical composition useful for increasing the endogenous production or release of growth hormone in a human or other animal which comprises a pharmaceutically acceptable carrier, a therapeutically effective amount of a compound, a salt or a prodrug according to claim 1 and a growth hormone secretagogue selected from the group consisting of GHRP-6, Hexarelin, GHRP-1, growth hormone releasing factor (GRF), IGF-1, IGF-2 and B-HT920 or an analog thereof.

30. A method for treating osteoporosis and/or frailty which comprises administering to a human or other animal in need of such treatment an amount of a compound, a salt or a prodrug according to claim 1 which is therapeutically effective in treating osteoporosis and/or frailty.

31. A method for treating diseases or conditions which may be treated by growth hormone which comprises administering to a human or other animal in need of such treatment an amount of a compound or a prodrug according to claim 1 which is therapeutically effective in promoting release of endogenous growth hormone.

32. A method according to claim 31 wherein the disease or condition is congestive heart failure, frailty associated with aging or obesity.

33. A method according to claim 32 wherein the disease or condition is congestive heart failure.

34. A method according to claim 33 wherein the disease or condition is frailty associated with aging.

35. A method for accelerating bone fracture repair, attenuating protein catabolic response after a major operation, reducing cachexia and protein loss due to acute or chronic illness, accelerating wound healing, or accelerating the recovery of burn patients or patients having undergone major surgery, which method comprises administering to a mammal in need of such treatment an amount of a compound, a salt or a prodrug according to claim 1 which is therapeutically effective in promoting release of endogenous growth hormone.

36. A method according to claim 35 wherein the method is for accelerating the recovery of patients having undergone major surgery.

37. A method according to claim 35 wherein the method is for accelerating bone fracture repair.

38. A method for improving muscle strength, mobility, maintenance of skin thickness, metabolic homeostasis or renal homeostasis, which method comprises administering to a human or other animal in need of such treatment an amount of a compound, a salt or a prodrug according to claim 1 which is therapeutically effective in promoting release of endogenous growth hormone.

39. A method for the treatment of osteoporosis and/or frailty which comprises administering to a human or other animal with osteoporosis and/or frailty therapeutically effective amounts of a bisphosphonate compound and a compound, a salt or a prodrug according to claim 1.

40. A method for the treatment of osteoporosis and/or frailty according to claim 39 wherein the bisphosphonate compound is alendronate.

41. A method for the treatment of osteoporosis and/or frailty according to claim 39 wherein the bisphosphonate compound is ibandronate.

42. A method for the treatment of osteoporosis and/or frailty which comprises administering to a human or other animal with osteoporosis and/or frailty therapeutically effective amounts of estrogen or Premarin® and a compound, a salt or a prodrug according to claim 1 and, optionally, progesterone.

43. A method for the treatment of osteoporosis and/or frailty which comprises administering to a human or other animal with osteoporosis and/or frailty therapeutically effective amounts of calcitonin and a compound, salt or prodrug according to claim 1.

44. A method to increase IGF-1 levels in a human or other animal deficient in IGF-1 which comprises administering to a human or other animal with IGF-1 deficiency a compound, a salt or a prodrug according to claim 1.

45. A method for the treatment of osteoporosis and/or frailty which comprises administering to a human or other animal with osteoporosis and/or frailty therapeutically effective amounts of an estrogen agonist or antagonist and a compound, a salt or a prodrug according to claim 1.

46. A method according to claim 45 wherein the estrogen agonist or antagonist is tamoxifen, droloxifene, raloxifene or idoxifene.

47. A method according to claim 45 wherein the estrogen agonist or antagonist is cis-6-(4-fluoro-phenyl)-5-[4-(2-piperidin-1-yl-ethoxy)-phenyl]-5,6,7,8-tetrahydro-naphthalene-2-ol;

(−)-Cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolodinoethoxy-3'-pyridyl]-2-phenyl-6-hydroxy-1,2,3,4-tetrahydro-naphthalene;

1-(4'-pyrrolidinoethoxyphenyl)-2-(4'-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydronaphthalene-2-ol; or 1-(4'-pyrrolidinolethoxyphenyl)-2-phenyl-6-hydroxy-1,2,3,4-tetrahydro-isoquinoline.

48. A method for enhancing growth and improving carcass quality of an animal other than humans which comprises administering to said animal a therapeutically effective amount of a compound, a salt or a prodrug according to claim 1.

49. A method for enhancing feed efficiency in an animal other than humans which comprises administering to said animal an therapeutically effective amount of a compound, a salt or a prodrug according to claim 1.

50. A method for increasing milk production in a female mammal which comprises administering to said female mammal a therapeutically effective amount of a compound, a salt or a prodrug according to claim 1.

51. A method for increasing piglet number, increasing pregnancy rate in sows, increasing viability of piglets, increasing weight of piglets or increasing muscle fiber size in piglets which comprises administering to a sow or piglet a therapeutically effective amount of a compound, a salt or a prodrug according to claim 1.

52. A method for increasing muscle mass, which method comprises administering to a human or other animal in need of such treatment a therapeutically effective amount of a compound, salt or a prodrug according to claim 1 which is therapeutically effective in promoting release of endogenous growth hormone.

53. A method for promoting growth in growth hormone deficient children which comprises administering to a growth hormone deficient child a compound, a salt or a prodrug according to claim 1 which is therapeutically effective in promoting release of endogenous growth hormone.

54. A method for the treatment or prevention of congestive heart failure, obesity or frailty associated with aging, which comprises administering to a human or other animal in need thereof therapeutically effective amounts of a functional somatostatin antagonist and a compound or a prodrug according to claim 1.

55. A method according to claim 54 wherein the functional somatostatin antagonist is an alpha-2 adrenergic agonist and the other animal is a dog, cat or a horse.

56. A method according to claim 55 wherein the alpha-2 adrenergic agonist is clonidine, xylazine, detomidine or medetomidine.

57. A method for treating insulin resistance in a mammal, which comprises administering to said mammal a therapeutically effective amount of a compound, a salt or prodrug according to claim 1.

58. A method accordig to claim 57 wherein the condition associated with insulin resistance is type I diabetes, type II diabetes, hyperglycemia, impaired glucose tolerance or an insulin resistant syndrome.

59. A method according to claim 57 wherein the condition associated with insulin resistance is associated with obesity or old age.

* * * * *